United States Patent
Deng et al.

(10) Patent No.: US 11,780,822 B2
(45) Date of Patent: Oct. 10, 2023

(54) HDAC INHIBITOR SOLID STATE FORMS

(71) Applicant: Viracta Subsidiary, Inc., Cardiff, CA (US)

(72) Inventors: Xiaohu Deng, San Diego, CA (US); Stewart Jones, Swindon (GB); David Slack, Rancho Santa Fe, CA (US)

(73) Assignee: VIRACTA SUBSIDIARY, INC., Cardiff, CA (US)

( * ) Notice: Subject to any disclaimer, the term of this patent is extended or adjusted under 35 U.S.C. 154(b) by 0 days.

(21) Appl. No.: 18/080,566

(22) Filed: Dec. 13, 2022

(65) Prior Publication Data

US 2023/0159494 A1 May 25, 2023

Related U.S. Application Data

(63) Continuation of application No. 17/830,881, filed on Jun. 2, 2022, which is a continuation of application No. PCT/US2020/063387, filed on Dec. 4, 2020.

(60) Provisional application No. 62/944,246, filed on Dec. 5, 2019.

(51) Int. Cl.
   *C07D 401/12* (2006.01)

(52) U.S. Cl.
   CPC ........ *C07D 401/12* (2013.01); *C07B 2200/13* (2013.01)

(58) Field of Classification Search
   CPC .................................................. C07D 401/12
   See application file for complete search history.

(56) References Cited

U.S. PATENT DOCUMENTS

| | | |
|---|---|---|
| 2010/0152155 A1 | 6/2010 | Moffat et al. |
| 2019/0091221 A1 | 3/2019 | Berenson et al. |
| 2019/0216818 A1 | 7/2019 | Woody |
| 2019/0290646 A1 | 9/2019 | Woody et al. |
| 2023/0023953 A1 | 1/2023 | Deng et al. |

FOREIGN PATENT DOCUMENTS

| | | |
|---|---|---|
| TW | 202134232 A | 9/2021 |
| WO | WO-2011113013 A2 | 9/2011 |
| WO | WO-2018013962 A1 | 1/2018 |
| WO | WO-2018013975 A1 | 1/2018 |
| WO | WO-2019140296 A1 | 7/2019 |
| WO | WO-2019201123 A1 | 10/2019 |
| WO | WO-2020243326 A1 | 12/2020 |
| WO | WO-2021071809 A1 | 4/2021 |
| WO | WO-2021113694 A1 | 6/2021 |
| WO | WO-2022094122 A1 | 5/2022 |
| WO | WO-2023003972 A1 | 1/2023 |

OTHER PUBLICATIONS

Banerji, U. et al., "A Phase I Pharmacokinetic and Pharmacodynamic Study of CHR-3996, an Oral Class I Selective Histone Deacetylase Inhibitor in Refractory Solid Tumors", Clin Cancer Res, 2012, vol. 18, No. 9, pp. 2687-2694.

Co-pending U.S. Appl. No. 18/080,570, inventors Deng; Xiaohu et al., filed Dec. 13, 2022.

Moffat, et al. Discovery of 2-(6-{[(6-fluoroquinolin-2-yl)methyl]amino}bicyclo[3.1.0]hex-3-yl)-N-hydroxypyrimidine-5-carboxamide (CHR-3996), a class I selective orally active histone deacetylase inhibitor. J Med Chem. Dec. 23, 2010;53(24):8663-78. Epub Nov. 16, 2010.

PCT/US2020/063387 International Search Report and Written Opinion dated Mar. 12, 2021.

Huang et al.: Separation and Purification of β-Carotene from Chlorophyll Factory Residues. Chemical Engineering & Technology 31(6):922-927. DOI:10.1002/ceat.200800039 (2008).

*Primary Examiner* — Brian E McDowell

(74) *Attorney, Agent, or Firm* — WILSON SONSINI GOODRICH & ROSATI

(57) ABSTRACT

The present disclosure relates to various solid-state forms of N-hydroxy 2-{6-[(6-fluoro-quinolin-2-ylmethyl)-amino]-3-aza-bicyclo[3.1.0]hex-3-yl}pyrimidine-5-carboxamide and methods of making the same. Such forms of N-hydroxy 2-{6-[(6-fluoro-quinolin-2-ylmethyl)-amino]-3-aza-bicyclo[3.1.0]hex-3-yl}pyrimidine-5-carboxamide are useful in preparation of pharmaceutical compositions and dosage forms for the treatment of cancer, immune disorders and inflammation.

20 Claims, 23 Drawing Sheets

| Angle (° 2θ) | Intensity (%) | Angle (° 2θ) | Intensity (%) |
|---|---|---|---|
| 7.2 | 4.1 | 23.6 | 2.8 |
| 11.3 | 0.9 | 24.1 | 12.9 |
| 14.4 | 4.1 | 24.5 | 4.1 |
| 14.6 | 4.5 | 25.2 | 2.5 |
| 15.9 | 37.2 | 26.7 | 13.6 |
| 17.2 | 1.7 | 27.1 | 5.7 |
| 17.7 | 1.6 | 27.5 | 6.7 |
| 18.0 | 3.1 | 28.3 | 1.9 |
| 18.2 | 3.4 | 28.8 | 3.8 |
| 19.6 | 7.1 | 29.1 | 38.2 |
| 21.2 | 24.0 | 29.9 | 2.4 |
| 21.7 | 100.0 | 30.8 | 3.8 |
| 23.2 | 29.6 | 31.6 | 4.0 |

FIG. 1B

| Angle (° 2θ) | Intensity (%) | Angle (° 2θ) | Intensity (%) |
|---|---|---|---|
| 7.1 | 19.0 | 23.2 | 5.4 |
| 9.9 | 10.0 | 24.3 | 3.3 |
| 14.1 | 10.1 | 24.6 | 24.1 |
| 14.3 | 12.9 | 25.5 | 38.3 |
| 15.7 | 29.4 | 26.0 | 53.3 |
| 16.0 | 3.9 | 26.3 | 3.1 |
| 16.4 | 3.6 | 27.8 | 14.0 |
| 17.3 | 32.9 | 27.9 | 15.4 |
| 19.3 | 4.4 | 28.3 | 33.0 |
| 19.9 | 100.0 | 29.0 | 18.8 |
| 20.4 | 4.3 | 29.4 | 5.9 |
| 21.1 | 48.3 | 30.4 | 5.4 |
| 21.3 | 8.3 | 31.6 | 4.5 |
| 22.4 | 33.6 | 31.9 | 5.3 |

FIG. 4B

| | |
|---|---|
| Crystal Size | 0.20 x 0.10 x 0.10 mm$^3$ |
| Radiation Type | Cu Kα (λ = 1.54184 Å) |
| Crystal system | triclinic |
| Space Group | P-1 |
| Cell Size | a = 6.30140(10) Å |
| | b = 12.6549(2) Å |
| | c = 12.7956(2) Å |
| | α = 101.4500(10)° |
| | β = 99.7920(10)° |
| | γ = 100.0240(10)° |
| Cell Volume | V = 962.41(3) Å$^3$ |
| Cell Formula Units | Z = 2 |
| Crystal Density | $D_c$ = 1.423 Mg/m$^3$ |
| Crystal F(000) | 432.0 |
| Absorption Coefficient mu | μ(Cu Kα) = 0.885 mm$^{-1}$ |
| Limiting Indices | -5 ≤ h ≤ 7 |
| | -15 ≤ k ≤ 14 |
| | -15 ≤ l ≤ 15 |
| Cell Measurement Temperature | T = 293 (2) K. |
| 2θ range for data collection | 7.298 to 133.18° |
| Goodness-of-fit on F^2 | 1.056 |
| Final R indices [I>2sigma(I)] | $R_1$ = 0.0356, $wR_2$ = 0.0977 |
| R indices (all data) | $R_1$ = 0.0392, $wR_2$ = 0.1003 |
| Largest diff. peak and hole | 0.18 and -0.20 e.Å$^{-3}$ |
| Reflections collected / unique | 17420 / 3379 [R(int) = 0.0238] |

FIG. 16

| | |
|---|---|
| Crystal Size | 0.20 x 0.10 x 0.10 mm$^3$ |
| Radiation Type | Cu Kα (λ = 1.54184 Å) |
| Crystal system | triclinic |
| Space Group | P-1 |
| Cell Size | a = 5.54380(10) Å |
| | b = 12.50580(10) Å |
| | c = 12.58730(10) Å |
| | α = 89.3430(10)° |
| | β = 84.5130(10)° |
| | γ = 81.2960(10)° |
| Cell Volume | V = 858.666(18) Å$^3$ |
| Cell Formula Units | Z = 2 |
| Crystal Density | $D_c$ = 1.525 Mg/m$^3$ |
| Crystal F(000) | 412.0 |
| Absorption Coefficient mu | μ(Cu Kα) = 0.921 mm$^{-1}$ |
| Limiting Indices | -6 ≤ h ≤ 6 |
| | -14 ≤ k ≤ 14 |
| | -14 ≤ l ≤ 14 |
| Cell Measurement Temperature | T = 99.98 (18) K. |
| 2θ range for data collection | 7.056 to 133.1° |
| Goodness-of-fit on F^2 | 1.074 |
| Final R indices [I>2sigma(I)] | $R_1$ = 0.0370, $wR_2$ = 0.0999 |
| R indices (all data) | $R_1$ = 0.0393, $wR_2$ = 0.1018 |
| Largest diff. peak and hole | 0.47 and -0.45 e.Å$^{-3}$ |
| Reflections collected / unique | 30813 / 3029 [R(int) = 0.0469] |

FIG. 18

HDAC INHIBITOR SOLID STATE FORMS

CROSS-REFERENCE TO RELATED APPLICATION

This application is a continuation of U.S. patent application Ser. No. 17/830,881, filed Jun. 2, 2022, which is a continuation of International Application No. PCT/US2020/063387, filed Dec. 4, 2020, which claims the benefit of U.S. Patent Application No. 62/944,246, filed Dec. 5, 2019, which are hereby incorporated by reference in their entirety.

BACKGROUND OF THE INVENTION

The present disclosure relates to a HDAC inhibitor compound used as viral inducing agent and pharmaceutical compositions of said compound, as well as the use of said compound in pharmaceutical compositions and medicine.

SUMMARY OF THE INVENTION

The present disclosure relates to various solid-state forms of N-hydroxy 2-{6-[(6-fluoro-quinolin-2-ylmethyl)-amino]-3-aza-bicyclo[3.1.0]hex-3-yl}pyrimidine-5-carboxamide and methods of making the same. Such forms of N-hydroxy 2-{6-[(6-fluoro-quinolin-2-ylmethyl)-amino]-3-aza-bicyclo[3.1.0]hex-3-yl}pyrimidine-5-carboxamide are useful in the treatment of cancer, immune disorders and inflammation.

Provided herein is a composition comprising crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

Provided herein is a composition comprising crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 15.9.

Provided herein is a pharmaceutical composition comprising crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide and at least one pharmaceutically acceptable excipient.

Provided herein is a composition comprising crystalline Form B of N-hydroxy 2-{6-[(6-fluoro-quinolin-2-ylmethyl)-amino]-3-aza-bicyclo[3.1.0]hex-3-yl}pyrimidine-5-carboxamide.

Provided herein is a composition comprising crystalline Form B of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 19.9.

Provided herein is a pharmaceutical composition comprising crystalline Form B of N-hydroxy 2-{6-[(6-fluoro-quinolin-2-ylmethyl)-amino]-3-aza-bicyclo[3.1.0]hex-3-yl}pyrimidine-5-carboxamide and at least one pharmaceutically acceptable excipient.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

FIG. 1B provides the tabulated values for the XRPD pattern reflections of crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

FIG. 4B provides the tabulated values for the XRPD pattern reflections of crystalline Form B of N-hydroxy 2-{6-[(6-fluoro-quinolin-2-ylmethyl)-amino]-3-aza-bicyclo[3.1.0]hex-3-yl}pyrimidine-5-carboxamide.

FIG. 16 shows the X-ray crystallographic data for crystalline Form A monohydrate.

FIG. 18 shows the X-ray crystallographic data for crystalline Form B.

DETAILED DESCRIPTION OF THE INVENTION

Figure 1A:
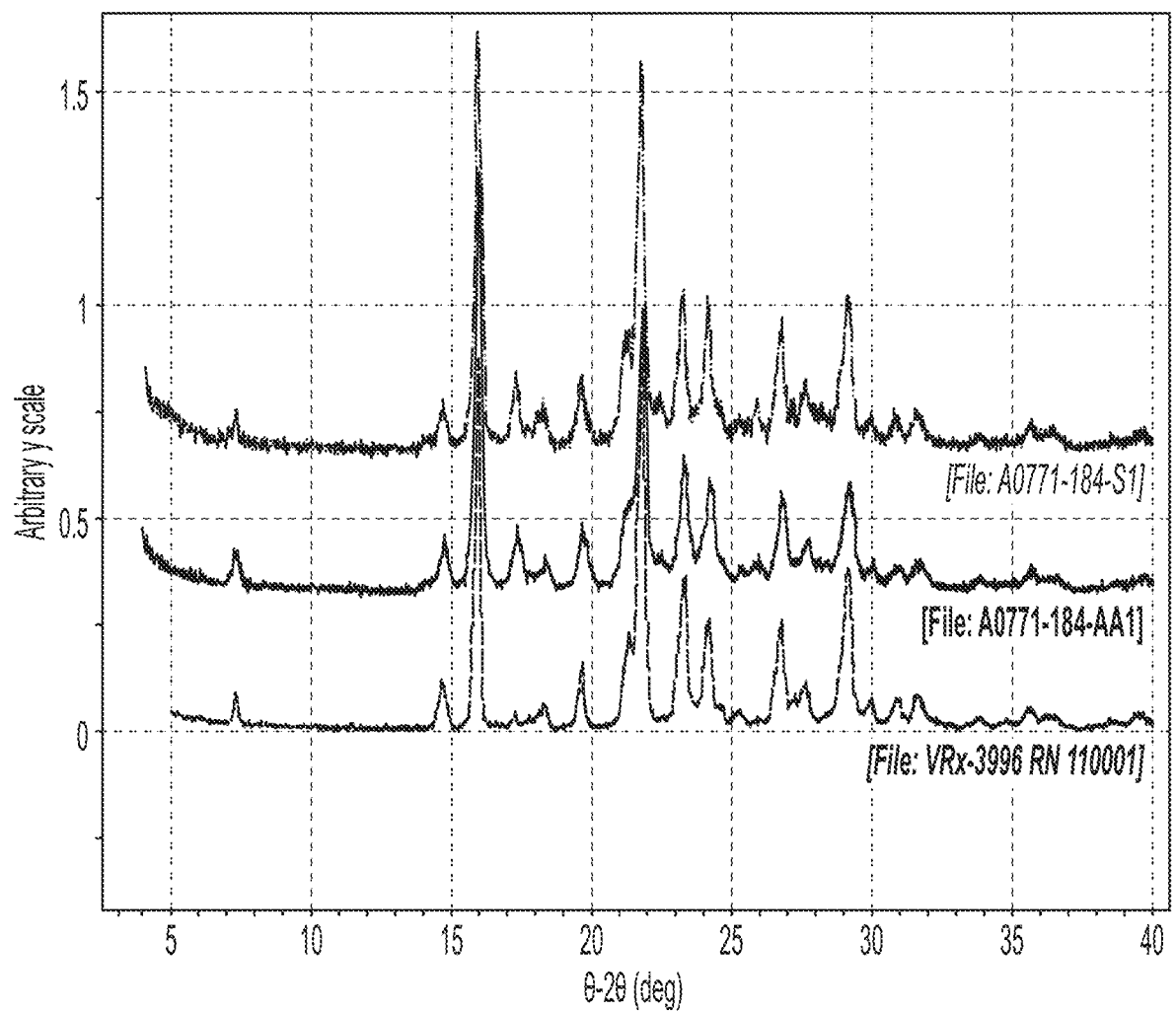
FIG. 1A shows the X-ray powder diffractogram (XRPD) of crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Compounds that are histone deacetylase (HDAC) inhibitors have the potential to provide therapeutically effective pharmaceutical compositions that would be expected to have beneficial and improved pharmaceutical properties for the treatment of epigenetic related conditions or disorders such as cancer and other proliferative disorders.

Discussed herein is N-hydroxy-2-{6-[(6-fluoro-quinolin-2-ylmethyl)-amino]-3-aza-bicyclo[3.1.0]hex-3-yl}pyrimidine-5-carboxamide and referred to herein as Compound 1. Compound 1 is also known as nanatinostat, VRx-3996, or CHR-3996. It has been previously described in patents and patent applications, e.g. U.S. Pat. No. 7,932,246 and U.S. patent application Ser. No. 15/959,482, each of which is incorporated by reference in their entirety.

Compound 1

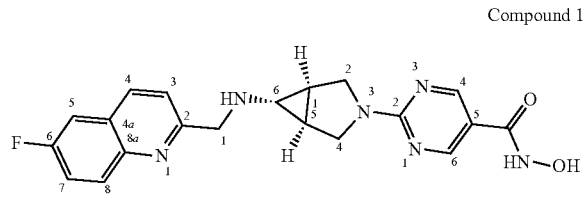 [SMILES: O=C(NO)c1cnc(N2C[C@@H]3[C@H](C2)[C@H]3NCc2ccc3cc(F)ccc3n2)nc1]

As a selective inhibitor of HDAC, Compound 1 is useful in the treatment of conditions in which HDAC has demonstrated a role in epigenetic regulation and pathology, such as cancer, immune disorders and inflammation. Two critical aspects in the development of Compound 1 as a useful therapy for such diseases and disorders are the discovery of practical methods for the preparation of Compound 1, and the discovery of pharmaceutically acceptable forms of Compound 1 and pharmaceutical compositions comprising said forms.

As used herein, the term "crystalline," "highly crystalline," "crystalline solid form," or "highly crystalline solid form" refers to a solid form which is substantially free of any amorphous solid state form. In some embodiments, the crystalline solid form is a single solid state form, e.g. crystalline hydrate Form A. One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

As used herein, the term "partially crystalline" or "partially crystalline material" refers to an ad-mixture of two or more solid state forms. In some embodiments, partially crystalline refers to an ad-mixture of an amorphous solid form and at least one crystalline solid form. Partially crystalline material is not amorphous.

In some embodiments, crystallinity of a solid form is determined by X-Ray Powder Diffraction (XRPD). In some embodiments, crystallinity of a solid form is determined by solid state NMR.

Crystalline Hydrate Form A of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

Provided herein is the crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 15.9.

Provided herein is the crystalline hydrate Form A is further characterized by X-ray diffraction pattern reflections at 2 theta values of 21.7, 29.1, and 23.2.

Provided herein is the crystalline hydrate Form A is further characterized by X-ray diffraction pattern reflections at 2 theta values of 21.7, 29.1, 23.2, 24.1, and 26.7.

Provided herein is the crystalline hydrate Form A is further characterized by at least one X-ray diffraction pattern reflection selected from a 2 theta value of 15.9, 21.7, 29.1, 23.2, 24.1, and 26.7.

Provided herein is the crystalline hydrate Form A is further characterized by at least two X-ray diffraction pattern reflections selected from a 2 theta value of 15.9, 21.7, 29.1, 23.2, 24.1, and 26.7.

Provided herein is the crystalline hydrate Form A is further characterized by at least three X-ray diffraction pattern reflections selected from a 2 theta value of 15.9, 21.7, 29.1, 23.2, 24.1, and 26.7.

Provided herein is the crystalline hydrate Form A is further characterized by at least four X-ray diffraction pattern reflections selected from a 2 theta value of 15.9, 21.7, 29.1, 23.2, 24.1, and 26.7.

Provided herein is the crystalline hydrate Form A is further characterized by at least five X-ray diffraction pattern reflections selected from a 2 theta value of 15.9, 21.7, 29.1, 23.2, 24.1, and 26.7.

Provided herein is the crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide exhibits the X-ray powder diffraction pattern as shown in FIG. 1.

Figure 2:
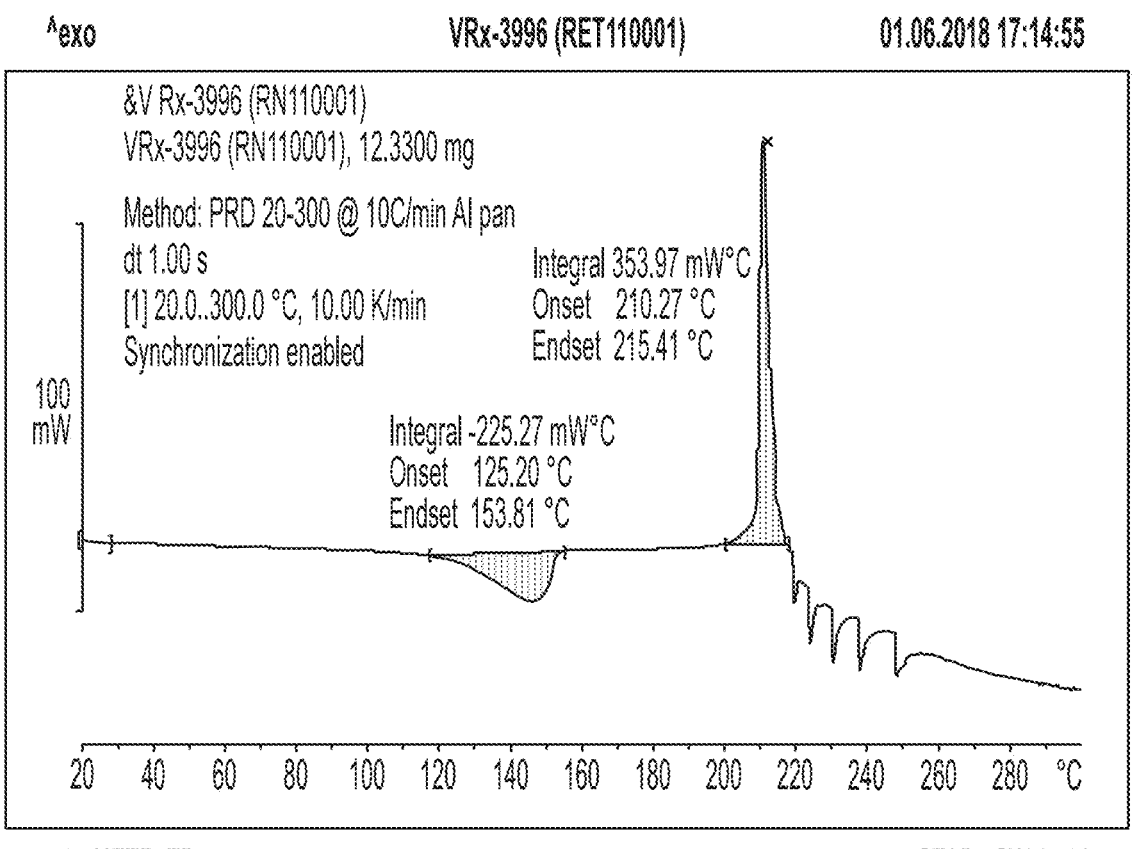
FIG. 2 shows the differential scanning calorimetry pattern of crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

Provided herein is the crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide exhibits the differential scanning calorimetry pattern as shown in FIG. 2.

Figure 3:
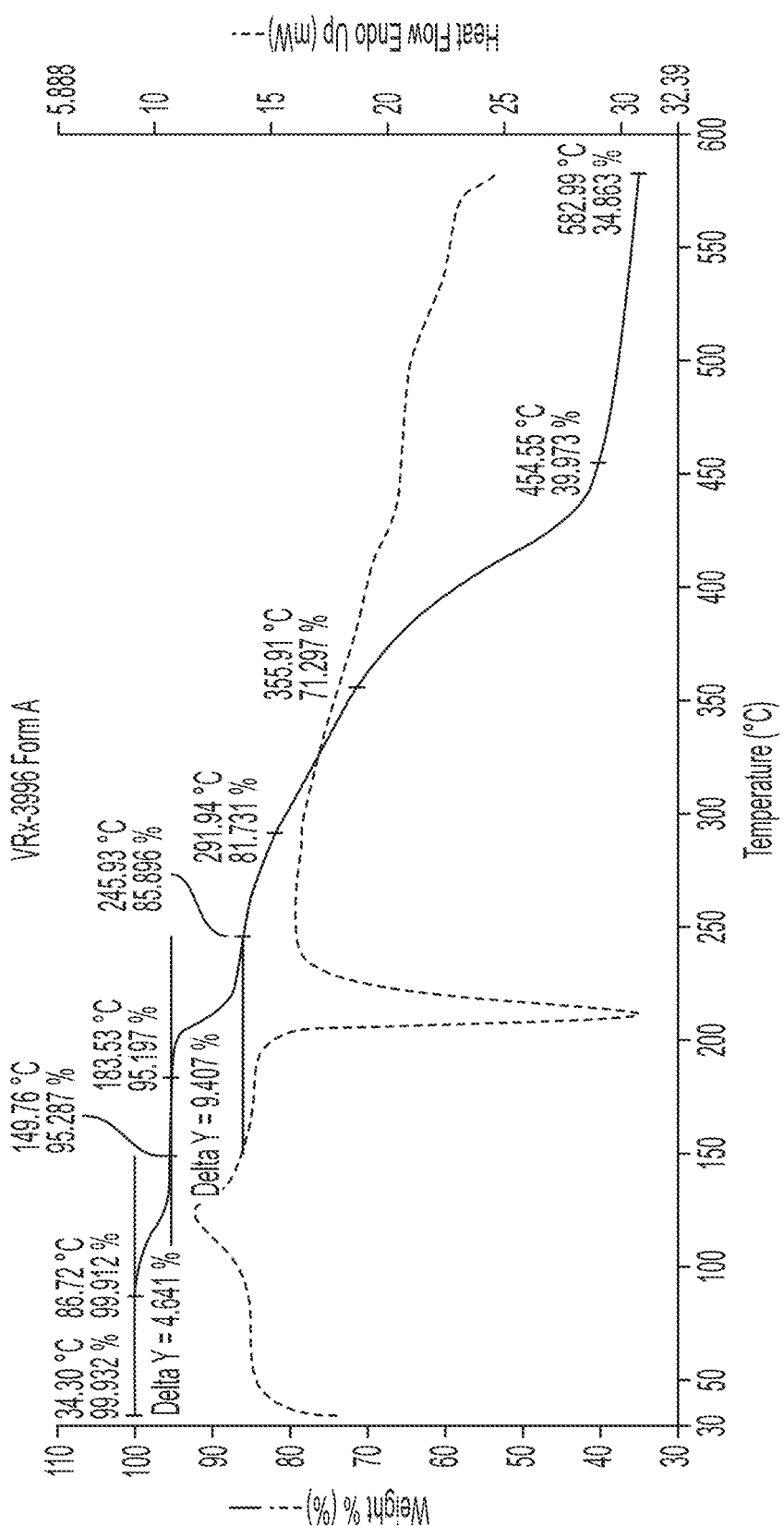
FIG. 3 shows the thermal gravimetric analysis pattern of crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

Provided herein is the crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide exhibits the thermogravimetric analysis pattern as shown in FIG. 3.

Crystalline Form B of N-Hydroxy 2-{6-[(6-fluoro-quinolin-2-ylmethyl)-amino]-3-aza-bicyclo[3.1.0]hex-3-yl}pyrimidine-5-carboxamide Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide.

Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide is characterized by an X-ray diffraction pattern reflection at a 2 theta value of 19.9.

Provided herein is the crystalline Form B is further characterized by X-ray diffraction pattern reflections at 2 theta values of 21.1, 17.3, 22.4, and 26.0.

Provided herein is the crystalline Form B is further characterized by X-ray diffraction pattern reflections at 2 theta values of 21.1, 17.3, 22.4, 26.0, 25.5, and 28.3.

Provided herein is the crystalline Form B is further characterized by at least one X-ray diffraction pattern reflection selected from a 2 theta value of 19.9, 21.1, 17.3, 22.4, 26.0, 25.5, 28.3, and 24.6.

Provided herein is the crystalline Form B is further characterized by at least two X-ray diffraction pattern reflections selected from a 2 theta value of 19.9, 21.1, 17.3, 22.4, 26.0, 25.5, 28.3, and 24.6.

Provided herein is the crystalline Form B is further characterized by at least three X-ray diffraction pattern reflections selected from a 2 theta value of 19.9, 21.1, 17.3, 22.4, 26.0, 25.5, 28.3, and 24.6.

Provided herein is the crystalline Form B is further characterized by at least four X-ray diffraction pattern reflections selected from a 2 theta value of 19.9, 21.1, 17.3, 22.4, 26.0, 25.5, 28.3, and 24.6.

Provided herein is the crystalline Form B is further characterized by at least five X-ray diffraction pattern reflections selected from a 2 theta value of 19.9, 21.1, 17.3, 22.4, 26.0, 25.5, 28.3, and 24.6.

Provided herein is the crystalline Form B is further characterized by at least six X-ray diffraction pattern reflections selected from a 2 theta value of 19.9, 21.1, 17.3, 22.4, 26.0, 25.5, 28.3, and 24.6.

Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide exhibits the X-ray powder diffraction pattern as shown in FIG. 4.

Figure 5:
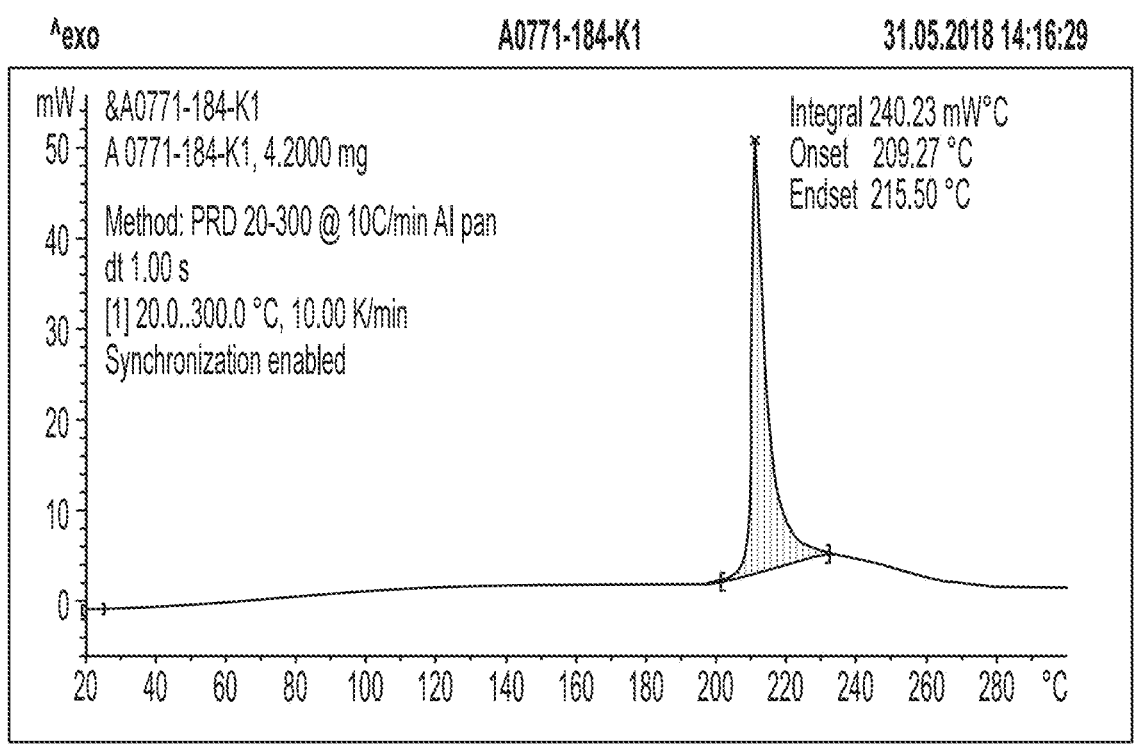
FIG. 5 shows the differential scanning calorimetry pattern of crystalline Form B of N-hydroxy 2-{6-[(6-fluoro-quinolin-2-ylmethyl)-amino]-3-aza-bicyclo[3.1.0]hex-3-yl}pyrimidine-5-carboxamide.

Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide exhibits the differential scanning calorimetry pattern as shown in FIG. 5.

Figure 6:
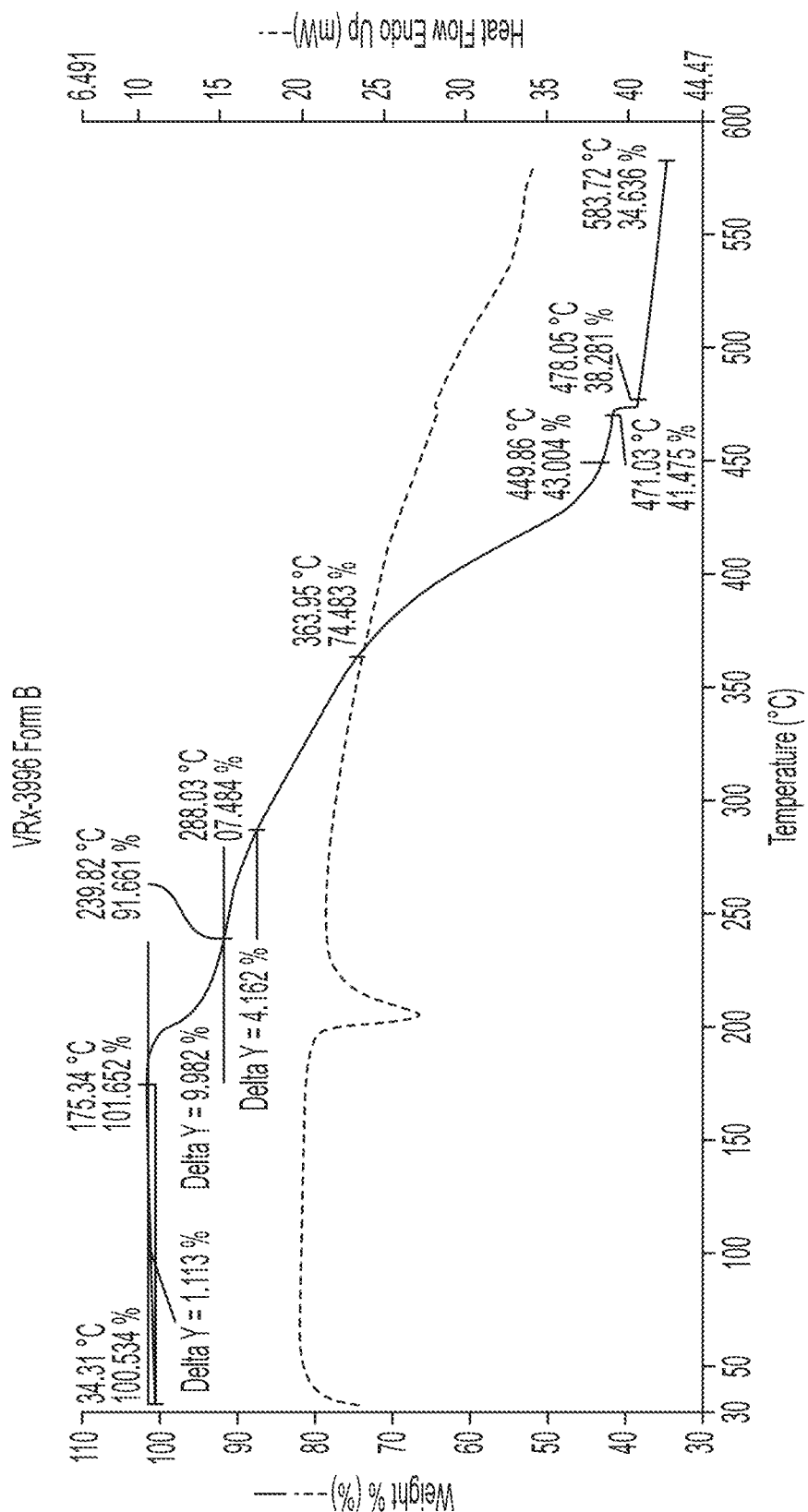
FIG. 6 shows the thermal gravimetric analysis pattern of crystalline Form B of N-hydroxy 2-{6-[(6-fluoro-quinolin-2-ylmethyl)-amino]-3-aza-bicyclo[3.1.0]hex-3-yl}pyrimidine-5-carboxamide.
Figure 7:
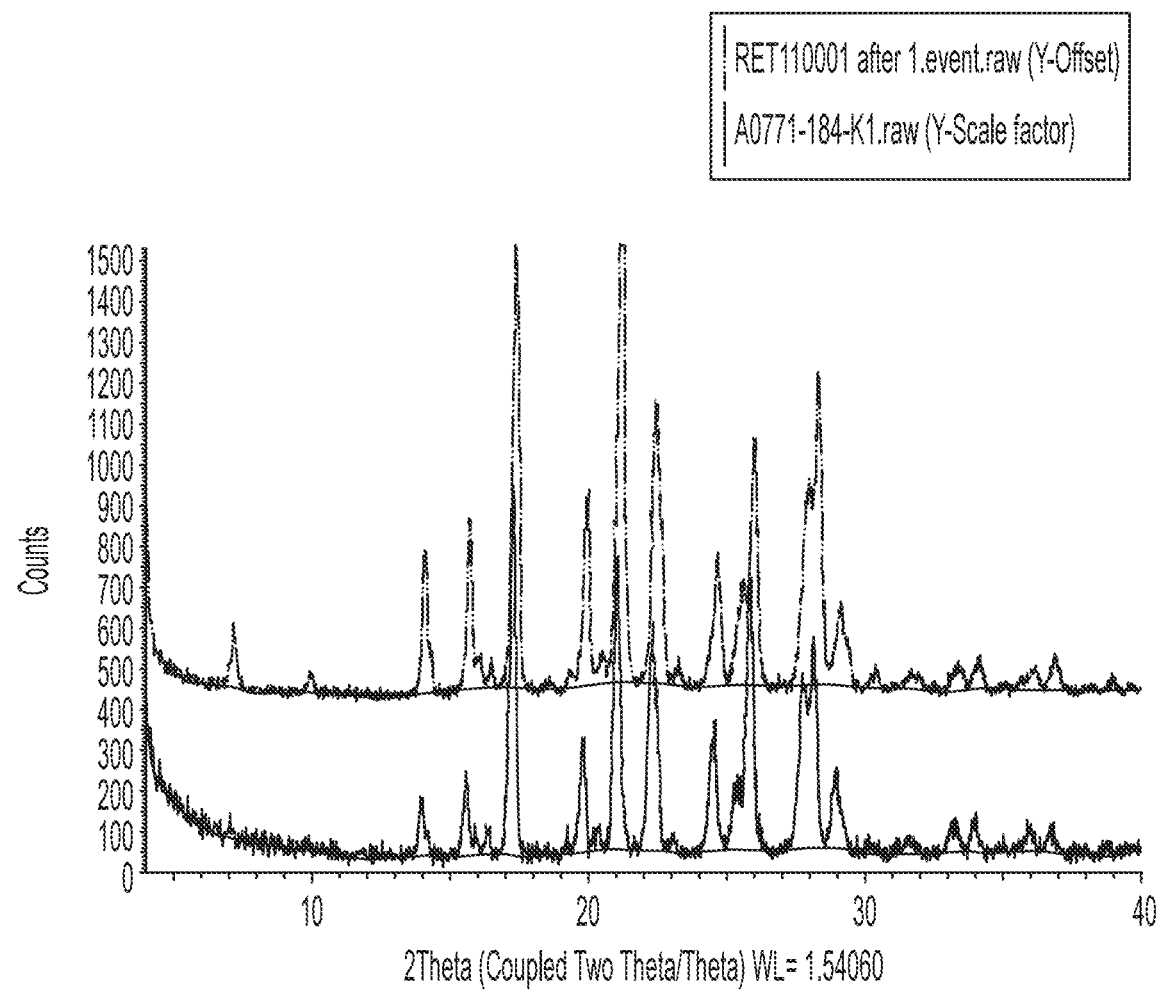
FIG. 7 shows the X-ray powder diffractogram of material prepared during the thermal investigation of Example 3.

Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide exhibits the thermogravimetric analysis pattern as shown in FIG. 6.

Provided herein is the crystalline Form B of N-hydroxy 2-{6-[(6-fluoro-quinolin-2-ylmethyl)-amino]-3-aza-bicyclo[3.1.0]hex-3-yl}pyrimidine-5-carboxamide is substantially free of water. Another embodiment provides a composition wherein substantially free means less than about 5% (w/w), less than about 3% (w/w), less than about 1% (w/w), less than about 0.5% (w/w), or less than about 0.2% (w/w).

Provided herein is the compound N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5%

(w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Pharmaceutical Compositions

Provided herein is a pharmaceutical composition comprising crystalline hydrate Form A of N-hydroxy 2-{6-[(6-fluoro-quinolin-2-ylmethyl)-amino]-3-aza-bicyclo[3.1.0] hex yl}pyrimidine-5-carboxamide, and one or more pharmaceutically acceptable excipients or carriers. In various embodiments, the pharmaceutical composition further comprises at least one pharmaceutically acceptable vehicle, carrier, diluent, or excipient, or a mixture thereof.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by an X-ray diffraction pattern reflection at a 2 theta value of 15.9, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by an X-ray diffraction pattern reflection at a 2 theta value of 15.9, 21.7, 29.1, and 23.2, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by an X-ray diffraction pattern reflection at a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by at least one X-ray diffraction pattern reflection selected from a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by at least two X-ray diffraction pattern reflections selected from a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide as characterized by at least three X-ray diffraction pattern reflections selected from a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex yl}pyrimidine-5-carboxamide as characterized by at least four X-ray diffraction pattern reflections selected from a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex yl}pyrimidine-5-carboxamide as characterized by at least five X-ray diffraction pattern reflections selected from a 2 theta value of 15.9, 21.7, 29.1, 23.2, 24.1, and 26.7, and one or more pharmaceutically acceptable excipients or carriers.

One embodiment provides a pharmaceutical composition comprising crystalline hydrate Form A of N-hydroxy 2-{6-[(6-fluoro-quinolin-2-ylmethyl)-amino]-3-aza-bicyclo [3.1.0]hex-3-yl}pyrimidine-5-carboxamide exhibiting the X-ray powder diffraction pattern as shown in FIG. 1, and one or more pharmaceutically acceptable excipients or carriers.

Provided herein is a pharmaceutical composition comprising crystalline Form B of N-hydroxy 2-{6-[(6-fluoro-quinolin-2-ylmethyl)-amino]-3-aza-bicyclo[3.1.0]hex-3-yl}pyrimidine-5-carboxamide, and one or more pharmaceutically acceptable excipients or carriers. In various embodiments, the pharmaceutical composition further comprises at least one pharmaceutically acceptable vehicle, carrier, diluent, or excipient, or a mixture thereof.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide as characterized by an X-ray diffraction pattern reflection at a 2 theta value of 19.9, and one or more pharmaceutically acceptable excipients or carriers.

One embodiment provides the pharmaceutical composition wherein the crystalline Form B is further characterized by X-ray diffraction pattern reflections at 2 theta values of 21.1, 17.3, 22.4, and 26.0.

One embodiment provides the pharmaceutical composition wherein the crystalline Form B is further characterized by X-ray diffraction pattern reflections at 2 theta values of 21.1, 17.3, 22.4, 26.0, 25.5, and 28.3.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide, wherein the crystalline Form B is further characterized by at least one X-ray diffraction pattern reflection selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex yl}pyrimidine-5-carboxamide, wherein the crystalline Form B is further characterized by at least two X-ray diffraction pattern reflections selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6- fluoro-quinolin-2-ylmethyl)-amino]-3-aza-bicyclo[3.1.0] hex yl}pyrimidine-5-carboxamide, wherein the crystalline Form B is further characterized by at least three X-ray diffraction pattern reflections selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide, wherein the crystalline Form B is further characterized by at least four X-ray diffraction pattern reflections selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide, wherein the crystalline Form B is further characterized by at least five X-ray diffraction pattern reflections selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide, wherein the crystalline Form B is further characterized by at least six X-ray diffraction pattern reflections selected from a 2 theta value of 19.9, 21.1, 17.3, 22.4, 26.0, 25.5, 28.3, and 24.6.

One embodiment provides a pharmaceutical composition comprising crystalline Form B of N-hydroxy 2-{6-[(6-fluoro-quinolin-2-ylmethyl)-amino]-3-aza-bicyclo[3.1.0] hex-3-yl}pyrimidine-5-carboxamide exhibits the X-ray powder diffraction pattern as shown in FIG. 4, and one or more pharmaceutically acceptable excipients or carriers.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment in accordance with the present disclosure. In terms of treatment protocols, it should be appreciated that the dosage to be administered will depend on several factors, including the particular agent that is administered, the route administered, the condition of the particular patient, etc. Determination of these parameters is well within the skill of the art. These considerations, as well as effective formulations and administration procedures are well known in the art and are described in standard textbooks.

The pharmaceutical compositions provided herein are formulated in various dosage forms for oral administration. These dosage forms can be prepared according to conventional methods and techniques known to those skilled in the art (see, *Remington: The Science and Practice of Pharmacy*, Loyd V., Jr, Allen, Ed., Pharmaceutical Press: New York, New York, 2002; Vol. 22).

As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, and effervescent or non-effervescent powders or granules. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents. In some embodiments, the oral dosage form is a tablet, capsule, or pill.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule, consists of two sections, one slipping over the other, thus completely enclosing the active ingredient. The soft elastic capsule is a soft, globular shell, such as a gelatin shell, which is plasticized by the addition of glycerin, sorbitol, or a similar polyol. The liquid, semisolid, and solid dosage forms provided herein may be encapsulated in a capsule. Suitable liquid and semisolid dosage forms include solutions and suspensions in propylene carbonate, vegetable oils, or triglycerides.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The examples and preparations provided below further illustrate and exemplify the polymorphs of the present disclosure and methods of preparing such polymorphs. It is to be understood that the scope of the present disclosure is not limited in any way by the scope of the following examples and preparations.

EXAMPLES

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

I. General Experimental Details—Instrument and Methodology Details

X-Ray Powder Diffraction (XRPD)

X-Ray powder diffraction (XRPD) analysis was carried out using a Bruker D2 Phaser powder diffractometer equipped with a LynxEye detector. The specimens underwent minimum preparation but, if necessary, they were lightly milled in a pestle and mortar before acquisition. The specimens were located at the center of a silicon sample holder within a 5 mm pocket (ca. 5 to 10 mg).

The samples were continuously spun during data collection and scanned using a step size of 0.02° two theta (2θ) between the range of 4° to 40° two theta. Data was acquired using either 3 minutes or 20 minutes acquisition methods. Data was processed using Bruker Diffrac.Suite.

Nuclear Magnetic Resonance (NMR)

$^1$H NMR Spectra were acquired using a Bruker 400 MHz spectrometer and data was processed using Topspin. Samples were prepared in DMSO-D6 at typical concentrations of 10 to 20 mg/mL and up to 50 mg/mL for $^1$H NMR w/w assay and calibrated to the corresponding non-deuterated solvent residual at 2.50 ppm.

$^1$H NMR w/w Assay: Assays (w/w) of compound 1 by $^1$H NMR spectroscopy were measured by the project chemist.

Internal standard maleic acid, (ca. 20 mg, F.W. 116.07) and compound 1 (ca. 20 mg) were dissolved in DMSO-D6 (2.0 mL) and the $^1$H NMR spectrum was acquired using an extended relaxation method.

The singlet attributed to the internal standard (maleic acid) at δ=6.3 ppm (s, 2H) and the doublet attributed to compound 1 at δ=8.6 ppm (d, 2H) were used to measure the assay.

Differential Scanning calorimetry (DSC)

A Mettler Toledo DSC 821 instrument was used for the thermal analysis operating with STARe™ software. The analysis was conducted in 404, open aluminum pans, under nitrogen and sample sizes ranged from 1 to 10 mg. Typical analysis method was 20 to 250 at 10° C./minute.

Thermo-Gravimetric Analysis (TGA)

The samples were analyzed in an open ceramic pan on a Perkin Elmer TG/DTA under a nitrogen purge (200 ml/min) at a scan rate of 100 C/min.

All DTA results are demonstrated with the Endo Up convention.

Infrared Spectroscopy

FT-IR Spectra were acquired using a PerkinElmer Spectrum One FT-IR spectrometer. Samples were analyzed directly using a universal ATR attachment in the frequency range 4000 to 600 cm$^{-1}$. Spectrums were processed using Spectrum CFD, vs. 4.0 PerkinElmer Instruments LLC.

Optical Microscopy

The instrument used for digital capture was an Olympus BX41 microscope with digital camera attachment. The magnification was ×100 and ×400. Samples were observed under plane polarized and cross polarized light.

Thermal Microscopy

The instrument used for digital capture was an Olympus BX41 microscope with digital camera and hot stage attachment. The magnification was ×100 and ×400. Samples were observed under plane polarized and cross polarized light.

LC-MS

Routine Liquid Chromatography-Mass Spectrometry (LC-MS) data were collected using a Micro Mass platform LCZ interfaced with: CTC Analytics liquid sample changer system, Waters 2487 dual λ absorbance detector and Agilent series 1100 binary pump.

The instrument used a ZMD quadrupole mass analyzer based detector and the mass separated ions were detected via a photomultiplier system. The ZMD quadrupole instrument was calibrated up to 2000 Da.

Dynamic Vapor Sorption (DVS)

Transfer about 10 mg of sample into a DVS and record the weight change with respect to the atmospheric humidity at 25° C.

Use the following parameters:

Equilibrium: dm/dt: 0.002%/min. (for min: 10 min and max: 180 min).

Drying: 0% RH for 120 min

RH (%) measurement step: 5%

RH (%) measurement step scope: 0-90-0%

The criteria for hygroscopicity evaluation are listed in below:

| Criteria for hygroscopicity evaluation | |
|---|---|
| Hygroscopicity Classification | Water Sorption Criterion* |
| Deliquescent | Sufficient water is absorbed to form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic | ΔW % < 0.2% |

*At 25 ± 1° C. and 80 ± 2% RH (European Pharmacopoeia 6.0)

II. Preparation and Characterization of Solid State Forms

Example 1: Crystallization Screen

Twenty-one 50 mg portions of compound 1 were charged to separate scintillation vials. To each vial was added the appropriate solvent and the suspensions were heated until full dissolution occurred. Stirring was suspended and the solutions were removed from the heat, allowed to cool slowly and left to stand undisturbed. Any solids that crystallized were isolated by filtration, de-liquored under a stream of nitrogen and dried at 40° C. under reduced pressure over ca 20 h (refer to Table 1).

TABLE 1

| Solvent component A (20 vol, 1000 μl) | Solvent component B | Solvent component B (μl) | Observation t = 24 h | Yield % th., not corr. | Input form (XRPD) | Output form (XRPD) |
|---|---|---|---|---|---|---|
| Acetone | Water | 1000 | solid | 86% | A | A |
| Acetonitrile | Water | 1020 | solid | 73% | A | A |
| Anisole | Hexafluoropropan-2-ol | 260 | solution | — | A | N/A |
| Butanol | Water | 1000 | solid | 90% | A | A + B |
| tert-Butylmethyl ether | Hexafluoropropan-2-ol | 1250 | solution | — | A | N/A |

TABLE 1-continued

| Solvent component A (20 vol, 1000 μl) | Solvent component B | Solvent component B (μl) | Observation t = 24 h | Yield % th., not corr. | Input form (XRPD) | Output form (XRPD) |
|---|---|---|---|---|---|---|
| Chlorobenzene | Hexafluoropropan-2-ol | 120 | solution | — | A | N/A |
| Cumene | Hexafluoropropan-2-ol | 220 | solution | — | A | N/A |
| 1,4-dioxane | Water | 190 | solid | 89% | A | A + B |
| Ethanol | Water | 1000 | solid | 94% | A | A |
| Ethyl acetate | Hexafluoropropan-2-ol | 1750 | solution | — | A | N/A |
| Isopropyl acetate | Hexafluoropropan-2-ol | 1650 | solution | — | A | N/A |
| Methanol | Water | 1000 | solid | 98% | A | D |
| Methyl acetate | Water | 1000 | solid | 93% | A | A |
| Methylethyl ketone | Water | 1000 | solid | 89% | A | A |
| Nitromethane | Hexafluoropropan-2-ol | 1000 | solution | — | A | N/A |
| 2-Propanol | Water | 1000 | solid | 94% | A | A |
| Propionitrile | Water | 1000 | solid | 79% | A | A |
| Tetrahydrofuran | Water | 210 | solid | 74% | A | A + B |
| Toluene | Hexafluoropropan-2-ol | 170 | solution | — | A | N/A |
| 2,2,2-trifluoroethanol | Water | 10 | solution | — | A | N/A |
| Trifluorotoluene | Hexafluoropropan-2-ol | 180 | solution | — | A | N/A |

Conclusions: Crystalline solids were obtained only in the presence of water. Single Form B and single Form C were not observed. A new hydrate form, designated Form D (a hemi-hydrate) was generated by crystallization from methanol/water. This was in contrast to the outcome from suspension equilibration that gave Form C (mono-hydrate), under the same solvent conditions (vide infra)

Figure 4A:
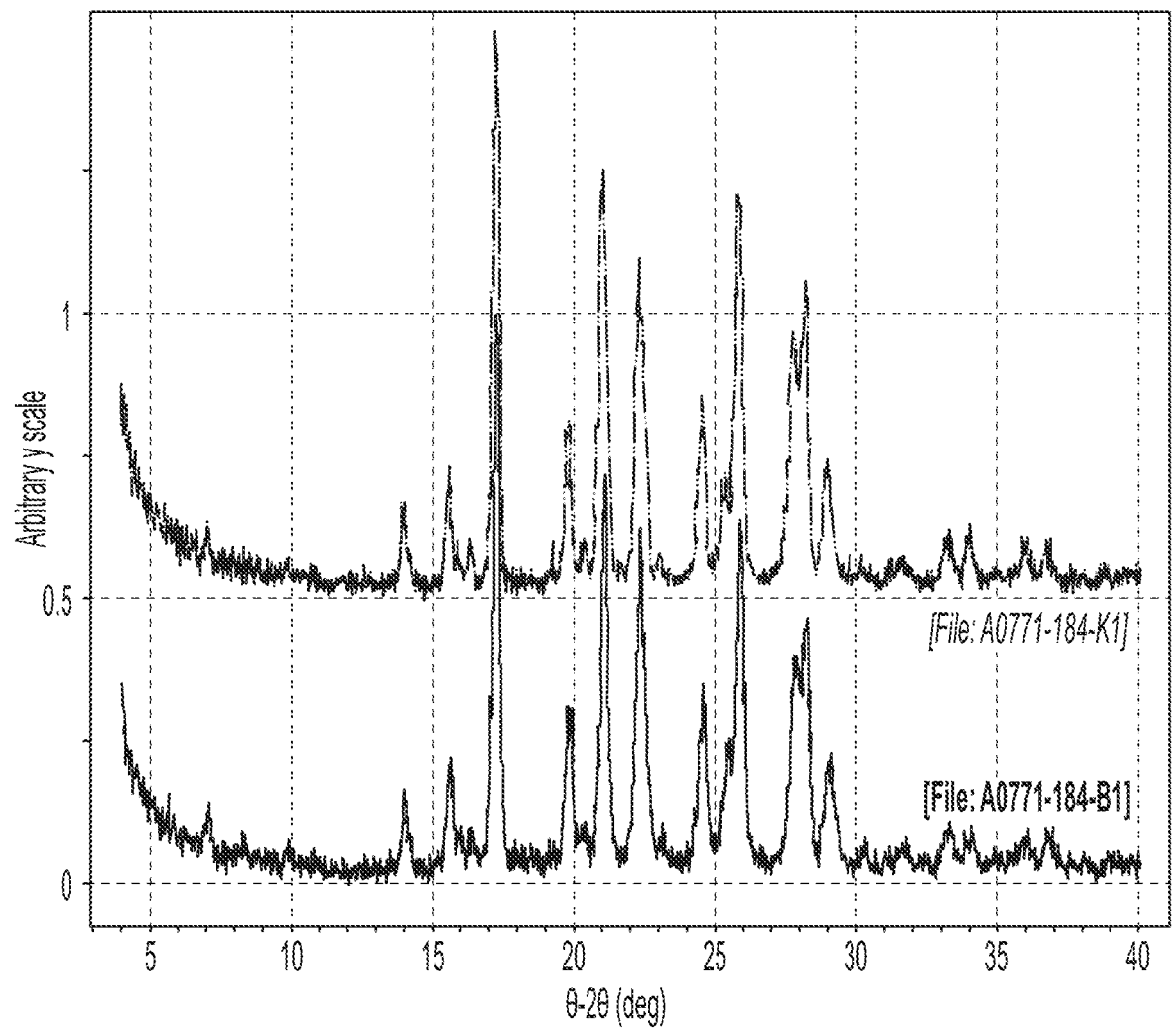
FIG. 4A shows the X-ray powder diffractogram of crystalline Form B of N-hydroxy 2-{6-[(6-fluoro-quinolin-2-ylmethyl)-amino]-3-aza-bicyclo[3.1.0]hex-3-yl}pyrimidine-5-carboxamide.

FIG. 1A provides the XRPD pattern of Form A. FIG. 1B provides the table of values for the XRPD pattern reflections of Form A. FIG. 4A provides the XRPD pattern of Form B. FIG. 4B provides the table of values for the XRPD pattern reflections of Form B.

Table 2 shows a general trend that crystallizations carried out under conditions of high water activity tend to favor the formation of hydrate forms, whilst solvent treatments at low water activity (i.e. under anhydrous conditions), promote the slow conversion of Form A into Form B (anhydrous). Table 2 shows Output Form from crystallization screen and anhydrous suspension equilibration study.

Example 2: Aqueous Suspension Equilibrations (20° C.)

Objective: Examine the effect of suspension equilibration of compound 1 under aqueous conditions (5% v/v) at ambient temperature and determine the physical form of the products.

Procedure: Compound 1 (ca 50 mg, 1.0 wt.) and the appropriate solvent (950 μl, 19 vol) and purified water (50 μl, 1.0 vol) were charged to separate vessels and stirred for 7 to 10 days at 20° C. After this time the products were cooled, isolated by filtration, washed with recycled maturation solvent, dried under reduced pressure at 20° C. and analyzed by XRPD for evidence of alternative crystalline forms.

Results: Table 3 provides the results of the aqueous suspension equilibration screen using Form A as the input.

TABLE 2

| Aqueous crystallization systems | Output from crystallization (XRPD) | Output from anhydrous maturations (XRPD) | Solvents Anhydrous suspension equilibration |
|---|---|---|---|
| Acetone/water (1/1 v/v, 40 vol) | A | A + B | Acetone |
| Acetonitrile/water (50/51 v/v, 40.4 vol) | A | B | Acetonitrile |
| Butanol/water (1/1 v/v, 40 vol) | A + B | A + B | Butanol |
| 1,4-dioxane/water (100/19 v/v, 23.8 vol) | A + B | A + B | 1,4-dioxane |
| Ethanol/water (1/1 v/v, 40 vol) | A | B | Ethanol |
| Methanol/water (1/1 v/v, 40 vol) | D | C | Methanol |
| Methyl acetate/water (1/1 v/v, 40 vol) | A | A + B | Methyl acetate |
| Methylethyl ketone/water (1/1 v/v, 40 vol) | A | A | Methylethyl ketone |
| 2-Propanol/water (1/1 v/v, 40 vol) | A | A + B | 2-Propanol |
| Propionitrile/water (1/1 v/v, 40 vol) | A | A + B | Propionitrile |
| Tetrahydrofuran/water (100/21 v/v, 24.2 vol) | A + B | A + B | Tetrahydrofuran |

TABLE 3

| Solvent | Observation (t = 7 day @ 20° C.) | Yield % th., not corr. | Input form (XRPD) | Output form (XRPD) | NMR data |
|---|---|---|---|---|---|
| Acetone | Suspension | 96% | A | A | Ethanol 0.75%; acetone 0.12% |
| Acetonitrile | Suspension | 93% | A | A | Ethanol 0.78%; acetonitrile 0.08% |
| Anisole | Suspension | 89% | A | A | Ethanol 0.80%; anisole 1.04% |
| Butanol | Suspension | 91% | A | A | Ethanol 0.70%; butanol not detected |
| tert-Butylmethyl ether | Gum | 53% | A | A | Ethanol 0.44%; tert-butylmethyl ether not detected |
| Chlorobenzene | Suspension | 78% | A | A | Ethanol 0.64%; chlorobenzene not detected |
| Cumene | Suspension | 84% | A | A | Ethanol 0.45%; cumene not detected |
| Dichloromethane | Suspension | 98% | A | A | Ethanol 0.85%; dichloromethane 0.45% |
| 1,4-dioxane | Suspension | 90% | A | A | Ethanol 0.71%; 1,4-dioxane not detected |
| DMSO | Feint suspension | 3% | — | — | Ethanol 0.72%; DMSO non-deuterated signals obscured |
| Ethanol | Suspension | 92% | A | A | Ethanol 0.96% |
| Ethyl acetate | Suspension | 93% | A | A | Ethanol 0.54%; ethyl acetate not detected |
| Ethyl ether | Gum | 70% | A | A | Ethanol 0.50%; ethyl ether not detected |
| Heptane | Gum | 72% | A | A | Ethanol 0.61%; heptane signals obscured |
| Hexafluoropropan-2-ol | Solution | — | — | — | N/A |
| Isopropyl acetate | Suspension | 90% | A | A | Ethanol 0.64%; isopropyl actetate not detected |
| Methanol | Suspension | 92% | A | A | Ethanol 0.493%; methanol 0.04%; by-product observed |
| Methyl acetate | Suspension | 93% | A | A | Ethanol 0.55%; methyl acetate 0.06% |
| Methylethyl ketone | Suspension | 91% | A | A | Ethanol 0.71%; methylethyl ketone 0.01% |
| Nitromethane | Suspension | 93% | A | A | Ethanol 0.78%; nitromethane 0.07% |
| 2-Propanol | Suspension | 91% | A | A | Ethanol 0.54%; methanol not detected |
| Propionitrile | Suspension | 93% | A | A | Ethanol 0.62%; propionitrile not detected |
| Tetrahydrofuran | Suspension | 93% | A | A | Ethanol 0.60%; THF signals obscured |
| Toluene | Gum | 89% | A | A | Ethanol 0.66%; toluene signals obscured |
| 2,2,2-trifluoroethanol | Suspension | 85% | A | A | Ethanol 0.66%; 2,2,2-trifluoroethanol not detected |
| Trifluorotoluene | Gum | 80% | A | A | Ethanol 0.77%; trifluorotoluene signals obscured |
| Water | Suspension | 90% | A | A | Ethanol 0.60%; water signals obscured |

Conclusions: The set of experiments was performed to determine whether or not the product (Form A) arises from endogenous starting material (i.e. unchanged) or exogenous Form A generated by crystallization during the maturation treatment. The following observations were made.

1. Under anhydrous conditions at 20° C., phase changes occurred (e.g. Form A to Form C in methanol) and this effect was exacerbated at elevated temperature 40° C.
2. Under aqueous conditions, no such changes were evident, implying that under conditions of high water activity Form A will remain as Form A, unless specifically dehydrated at higher temperature
3. Gumming was apparent under certain circumstances. The products from the solid/liquid phase separation were still consistent with Form A
4. The evidence is compelling that Form A and compound 1 solution are in dynamic equilibrium and as new Form A is seeded and crystallizes, authentic Form A dissolves to take its place, eventually resulting in turnover of the original starting material phase into the same indistinguishable product phase
5. The input material Form A contained ethanol 0.2% w/w, the impact of solvent treatment at high water activity on the level of ethanol was assessed by $^1$H NMR and did not control the level of ethanol Example 3: Thermal Investigations of Form A Objective: Examine the two events observed during DSC analysis of Form A.

Figure 9:
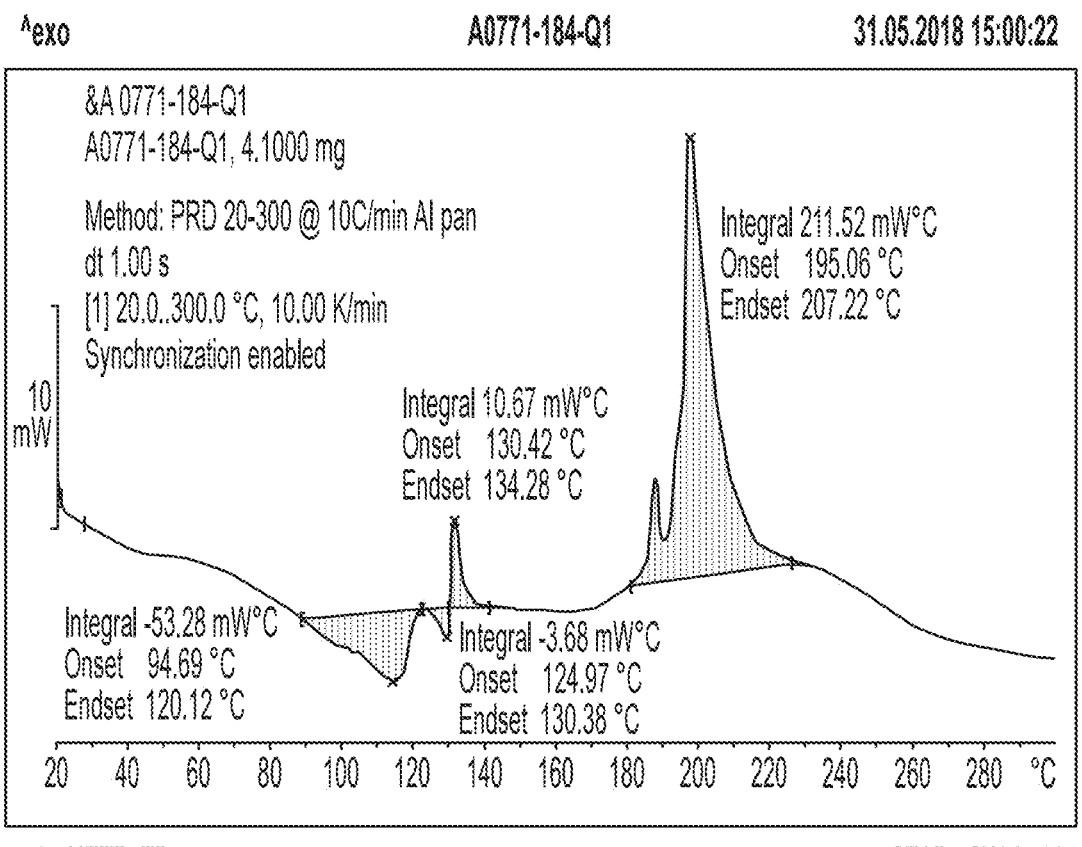
FIG. 9 shows the differential scanning calorimetry pattern of crystalline Form C of N-hydroxy 2-{6-[(6-fluoro-quinolin-2-ylmethyl)-amino]-3-aza-bicyclo[3.1.0]hex-3-yl}pyrimidine-5-carboxamide.

Procedure: First experiment-A sample of compound 1 Form A containing 5.1% w/w water and 0.2% w/w ethanol (ca. 16 mg) was heated at a rate of +10° C./min from 20 to 160° C. to include the first endothermic event and exclude the second event (refer to FIG. 2). The content of the spent crucible was expressed, the residue was analyzed by XRPD and the diffraction pattern was consistent with Form B (refer to FIG. 9). Second experiment—a sample of compound 1 From A (ca. 5 mg) was heated at a rate of +10° C./min from 20 to 230° C. to include the second event, cooled, analyzed by $^1$H NMR and consistent with extensive degradation.

The effect of elevated humidity (75 to 80% RH at 18 to 23° C.) on the thermally dehydrated Form A residue from the preceding experiment, was examined via conventional desiccator analysis at equilibrium humidity. Compound 1 Form A (ca. 16 mg) was heated at a rate of +10° C./min from 20 to 160° C. to include the first endothermic event and exclude the second event (see FIG. 2). The content of the spent crucible was exposed to 75 to 80% RH (relative humidity) at 18 to 23° C. for 72 h. The corresponding weight changes were recorded and the internal conditions of the humidity enclosures were monitored. The absorbent increased in weight (refer to Table 4), but this was not accompanied by a significant change in the diffraction pattern, or dehydration event by DSC.

stirred for 7 to 10 days at 20° C. and 40° C. After this time the products were cooled, isolated by filtration, washed with recycled maturation solvent, dried under reduced pressure at 20° C. and analyzed by XRPD for evidence of alternative crystalline forms.

Results: Results from anhydrous suspension equilibration screen at 20° C., compared to the parallel screen performed at 40° C. using Form A as the input are provided in Table 5.

TABLE 4

| Reference (input) | Input Form designation (XRPD) | RH 75-80%, 0 h @ 18-23° C. | RH 75-80%, 1 h @ 18-23° C. | RH 75-80%, 24 hr @ 18-23° C. | RH 75-80%, 72 hr @ 18-23° C. | Output Form designation (XRPD) |
|---|---|---|---|---|---|---|
| Form A after heating up to 160° C. Δwt. Percent | Isostructural Form B | 0.0% w/w | 14.6% w/w | 13.2% w/w | 14.6% w/w | Isostructural Form B |

The following observations were made:
1. Form A (hydrate) was dehydrated by heating above 160° C. The resultant dehydrate was consistent with Form B.
2. Dehydration of Form A does not proceed via a single component phase to generate an isomorphic dehydrate, that is common with channel and non-stoichiometric hydrates, instead the dehydration of Form A proceeds via a two component phase to generate non-reversible Form A dehydrate that is isostructural with Form B.
3. This implies that for Form A to release its water of crystallization the crystal has to first reorganize and liberate water in the process.
4. Form A dehydrate (isostructural with Form B) was exposed to constant elevated relative humidity and did not revert back to Form A; weight uptake of the absorbent was observed and this was attributed to monolayer wetting or similar reversible moisture sorption processes, no evidence for uptake of strongly bound water was evident from the DSC analyses.
5. Therefore, Form A dehydrates into Form B and Form B does not revert back to Form A under high water activity, and Form A is likely to be a stoichiometric hydrate, that can only dehydrate by reorganizing its crystal structure.
6. The large exothermic event observed post heating to 200° C. was consistent with degradation, and was confirmed by $^1$H NMR.
7. Dehydration was consistent with a weight loss transition of 4.6% w/w by TG analysis, consistent with the mono-hydrate.

Example 4: Suspension Equilibrations of Form A at 20° C. and 40° C.

Objective: Examine the effect of suspension equilibration of compound 1 under anhydrous conditions at 20° C. and 40° C. and determine the physical form of the products. Compare these results of the parallel equilibration screens and determine if transitions were operable within this temperature range.

Procedure: Compound 1 (ca 50 mg, 1.0 wt) and the appropriate solvent (1000 μl, 20 vol) were charged to separate vessels and two parallel banks of experiments were

TABLE 5

| Solvent | Input form @ 20 & 40° C. (XRPD) | Output form @ 20° C. (XRPD) | Output form @ 40° C. (XRPD) |
|---|---|---|---|
| Acetone | A | A | A + B |
| Acetonitrile | A | A | B |
| Anisole | A | A | A + B |
| Butanol | A | A | A + B |
| tert-Butylmethyl ether | A | A | A + B |
| Chlorobenzene | A | A | A + B |
| Cumene | A | A | A + B |
| Dichloromethane | A | A | A + B |
| 1,4-dioxane | A | A | A + B |
| DMSO | A | N/A | N/A |
| Ethanol | A | A | B |
| Ethyl acetate | A | A | A + B |
| Ethyl ether | A | A | A + B |
| Heptane | A | A | A + B |
| Hexafluoropropan-2-ol | A | N/A | N/A |
| Isopropyl acetate | A | A | A + B |
| Methanol | A | C | C |
| Methyl acetate | A | A | A + B |
| Methylethyl ketone | A | A | A |
| Nitromethane | A | A | A + B |
| 2-Propanol | A | A | A + B |
| Propionitrile | A | A | A + B |
| Tetrahydrofuran | A | A | A + B |
| Toluene | A | A | A |
| 2,2,2-trifluoroethanol | A | N/A | N/A |
| Trifluorotoluene | A | A | A + B |
| Water | A | N/A | A |

Figure 8:
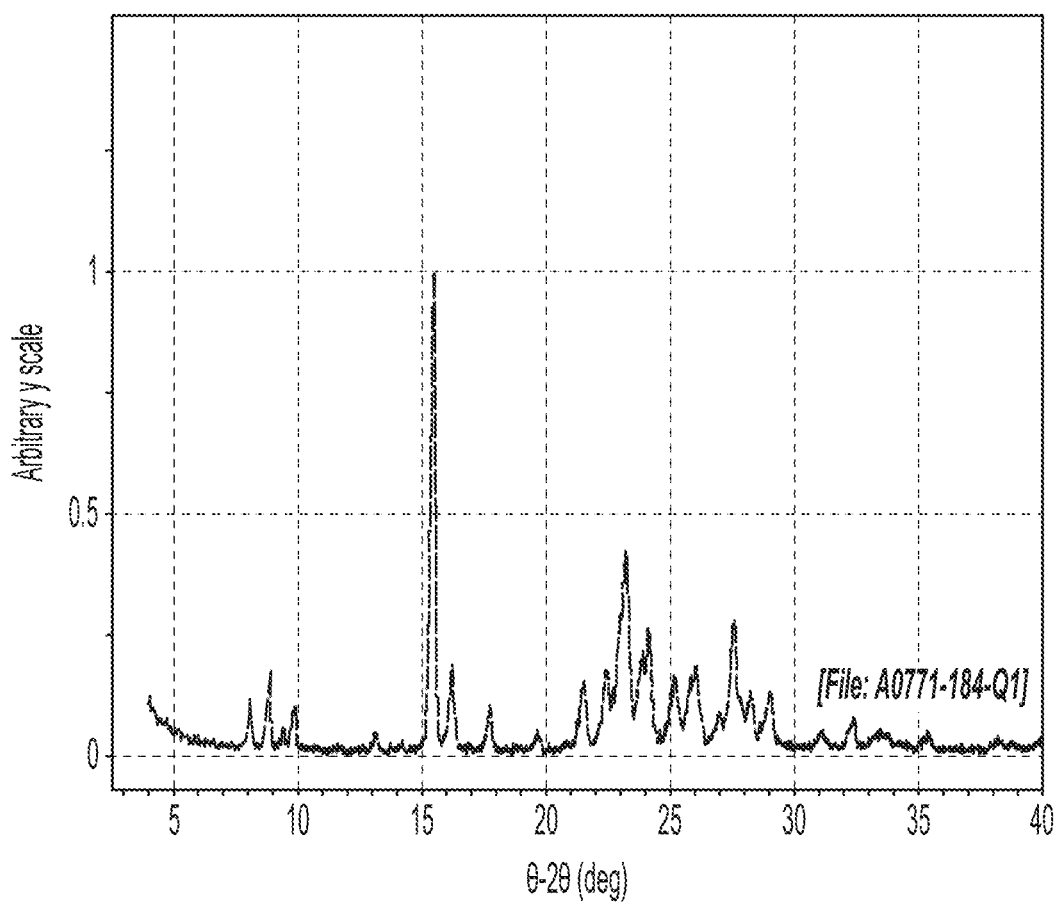
FIG. 8 shows the X-ray powder diffractogram of crystalline Form C of N-hydroxy 2-{6-[(6-fluoro-quinolin-2-ylmethyl)-amino]-3-aza-bicyclo[3.1.0]hex-3-yl}pyrimidine carboxamide.

The following observations were made:
1. The majority of the products isolated were consistent with mixtures of Form A and Form B in varying proportions.
2. Two additional distinct forms were also identified: Form B and Form C (see FIG. 8).
3. The slurry bridge transition for Form A (hydrate) conversion into Form B (anhydrous) was able to take place between 20° C. and 40° C. for the majority of solvents trialed.
4. At 20° C., the majority of the products isolated were consistent with Form A. Form A is most likely generated via dissolution and crystallization under the maturation conditions and is unlikely to be authentic starting material. Evidence for this hypothesis is supported by the dissolution of Form A and crystallization into Form C from methanol. Similar dissolutions ought to occur in in solvents in which the API exhibits similar solubility; however, in these cases only Form A crystallizes from solution.

Example 5: Thermal Investigations of Form C

Objective: Examine multiple thermal events of Form C containing 6.3% w/w/water and <0.1% w/w methanol.

Procedure: First event: A sample of compound 1 Form C (ca. 7 mg) was heated at a rate of +10° C./min from 20 to 120° C. to include the first endothermic event (refer to FIG. 9). The content of the spent crucible was expressed, the residue was analyzed by XRPD and the diffraction pattern was compared to the input diffraction pattern.

Third event: A sample of compound 1 Form C (ca. 5 mg) was heated at a rate of +10° C./min from 20 to 150° C. to include the multiple thermal events (refer to FIG. 9). The content of the spent crucible was expressed, the residue was analyzed by XRPD and the diffraction pattern was compared to the input diffraction pattern.

Figure 10:
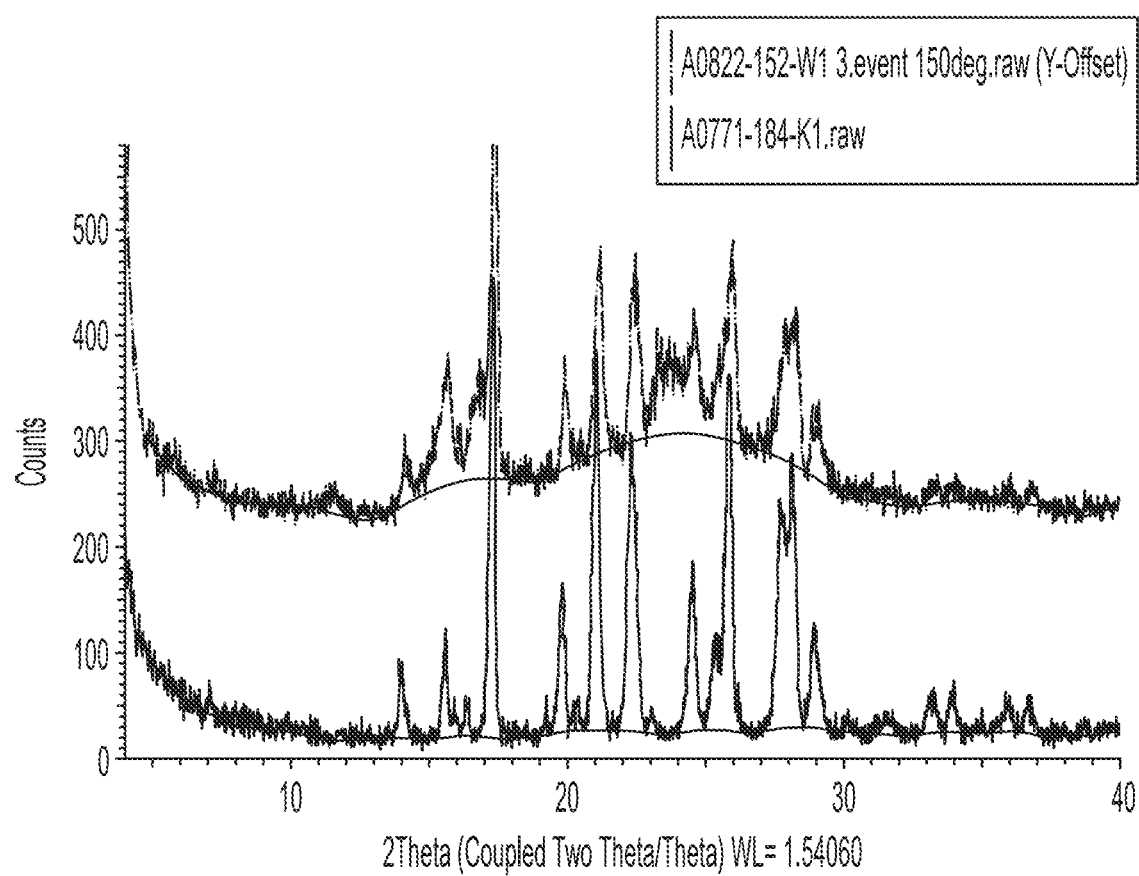
FIG. 10 shows the X-ray powder diffractogram of material prepared during the thermal investigation of Example 5.

The following observations were made:
1. Form C was heated above 120° C. and compared with the input. The resultant diffraction patterns (see FIG. 10) were consistent and suggest that the Form C dehydrate is consistent with an isomorphic desolvate/dehydrate, i.e. dehydration proceeds via a single phase
2. Form C (hydrate) was heated above 150° C., which first dehydrated the specimen into isomorphic Form C, after which it underwent melt and cold crystallization events and converted into isostructural Form B.
3. Therefore, both Form A and Form C, when heated eventually generate isostructural Form B. Form A is likely to be a stoichiometric hydrate (i.e. hydration stoichiometry remains approximately constant irrespective of the external conditions and loss of water generates a new phase). Form C is likely to be a non-stoichiometric hydrate and is able to exhibit variable water contents depending on the local environment, all the way down to 0%, at which point it presents as an isomorphic desolvate/dehydrate.
4. TG Analysis exhibited a weight loss transition of 3.2% w/w that corresponded to water release without form change, the weight loss transition was lower than the KF measured value of the solubilized material (6.3% w/w).

Example 6: Thermal Investigations of Form E

Figure 11:
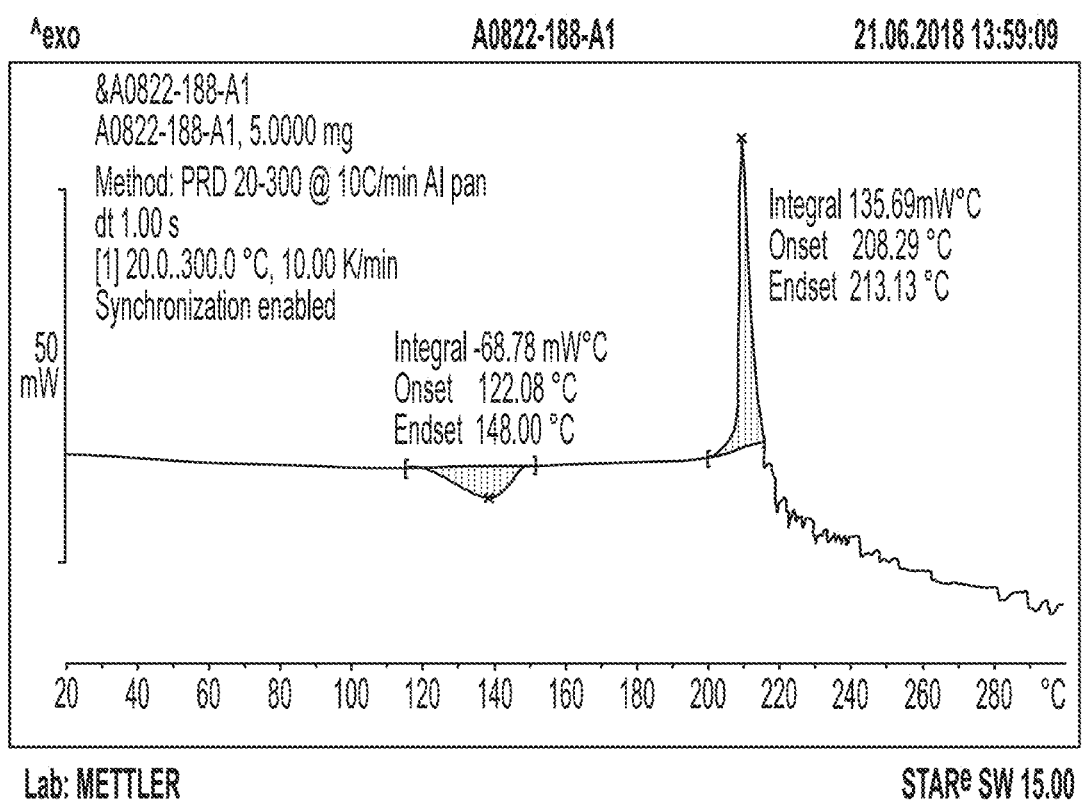
FIG. 11 shows the differential scanning calorimetry pattern of crystalline Form E of N-hydroxy 2-{6-[(6-fluoro-quinolin-2-ylmethyl)-amino]-3-aza-bicyclo[3.1.0]hex-3-yl}pyrimidine-5-carboxamide.

Objective: Determine the nature of the event that occurs between 120 to 190° C. (see FIG. 11). Establish if the event is accompanied by a phase change by XRPD.

Figure 12:
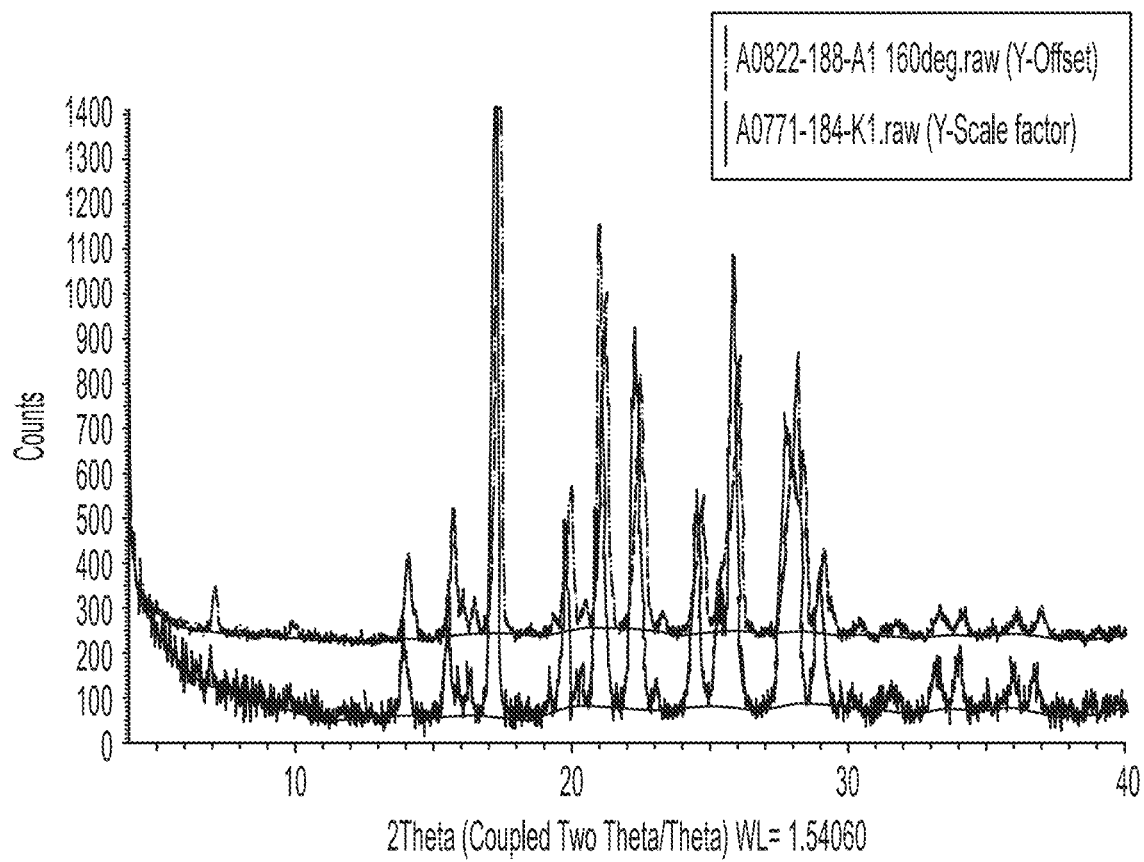
FIG. 12 shows the X-ray powder diffractogram of crystalline Form E of N-hydroxy 2-{6-[(6-fluoro-quinolin-2-ylmethyl)-amino]-3-aza-bicyclo[3.1.0]hex-3-yl}pyrimidine-5-carboxamide.
Figure 13A:
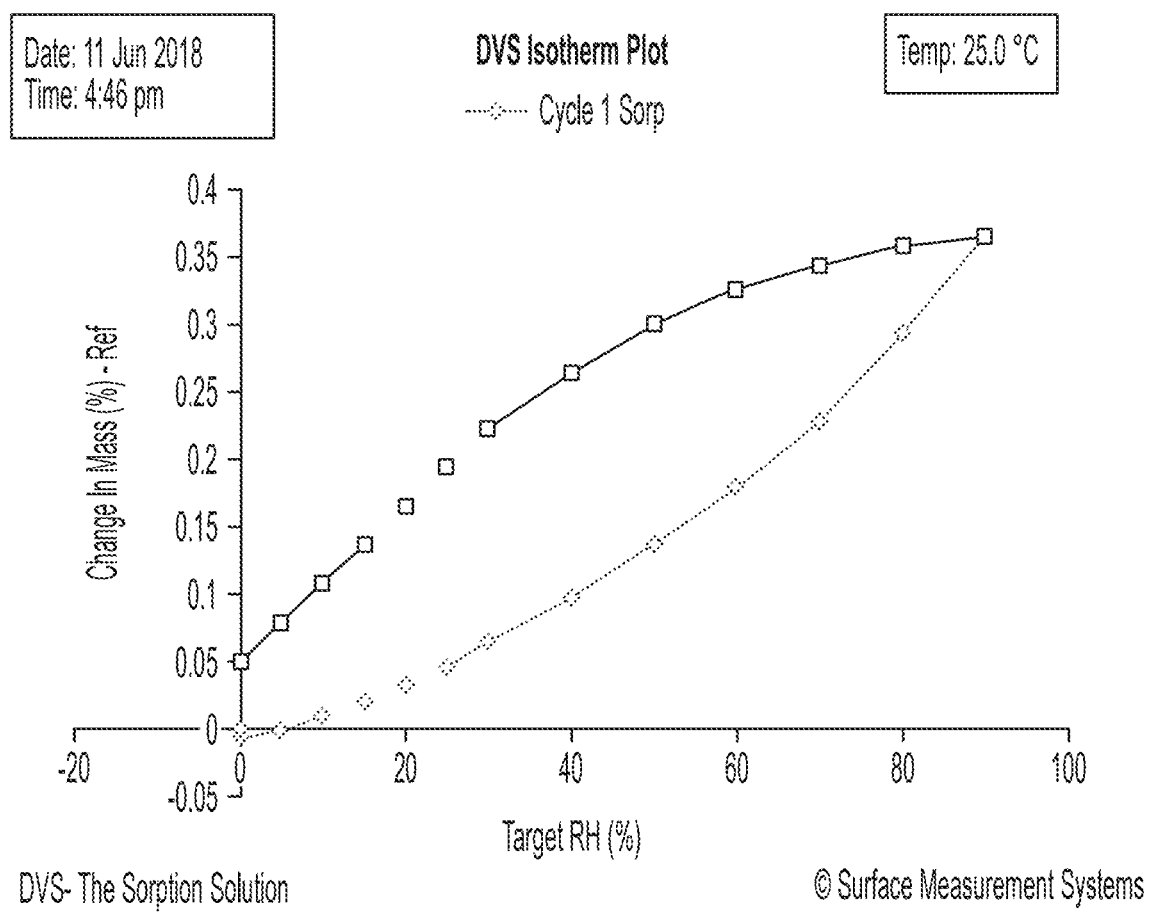
FIG. 13A and FIG. 13B show the DVS plot of crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.
Figure 13B:
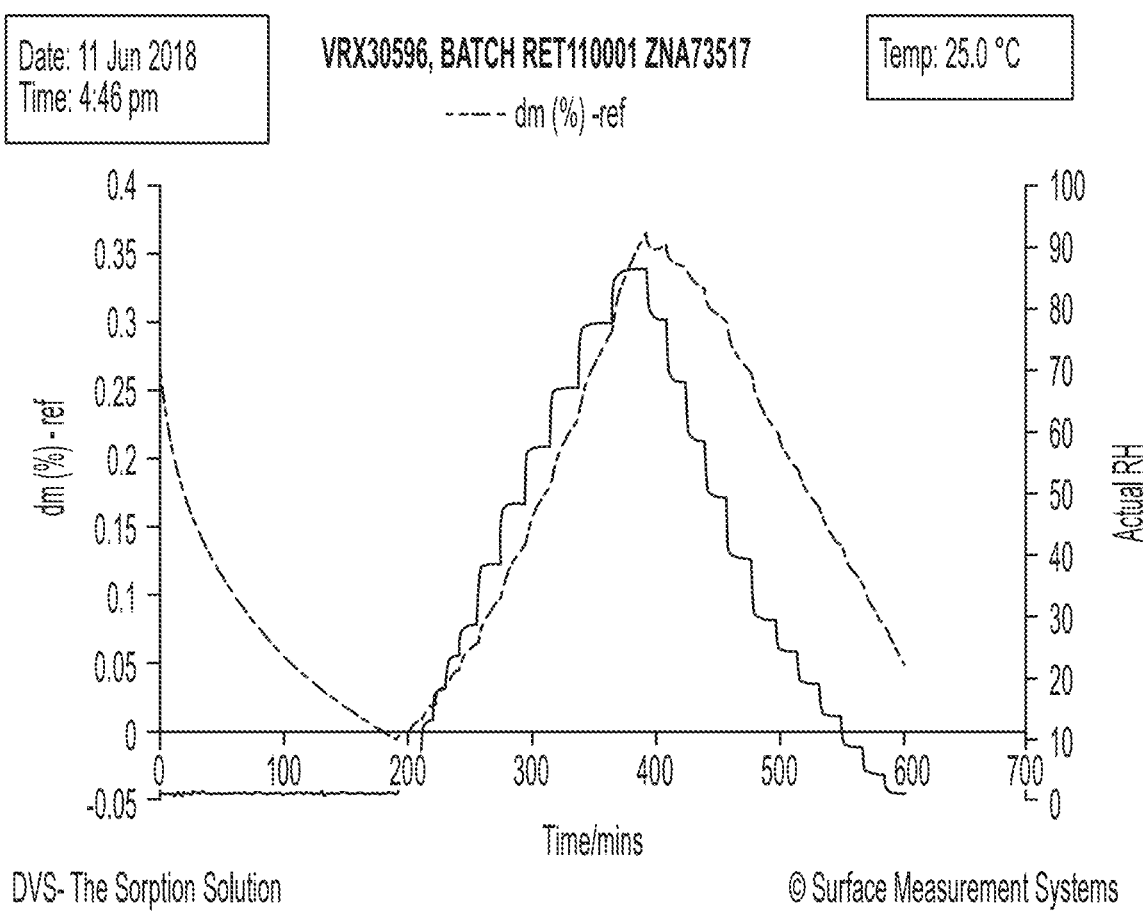
Figure 14A:
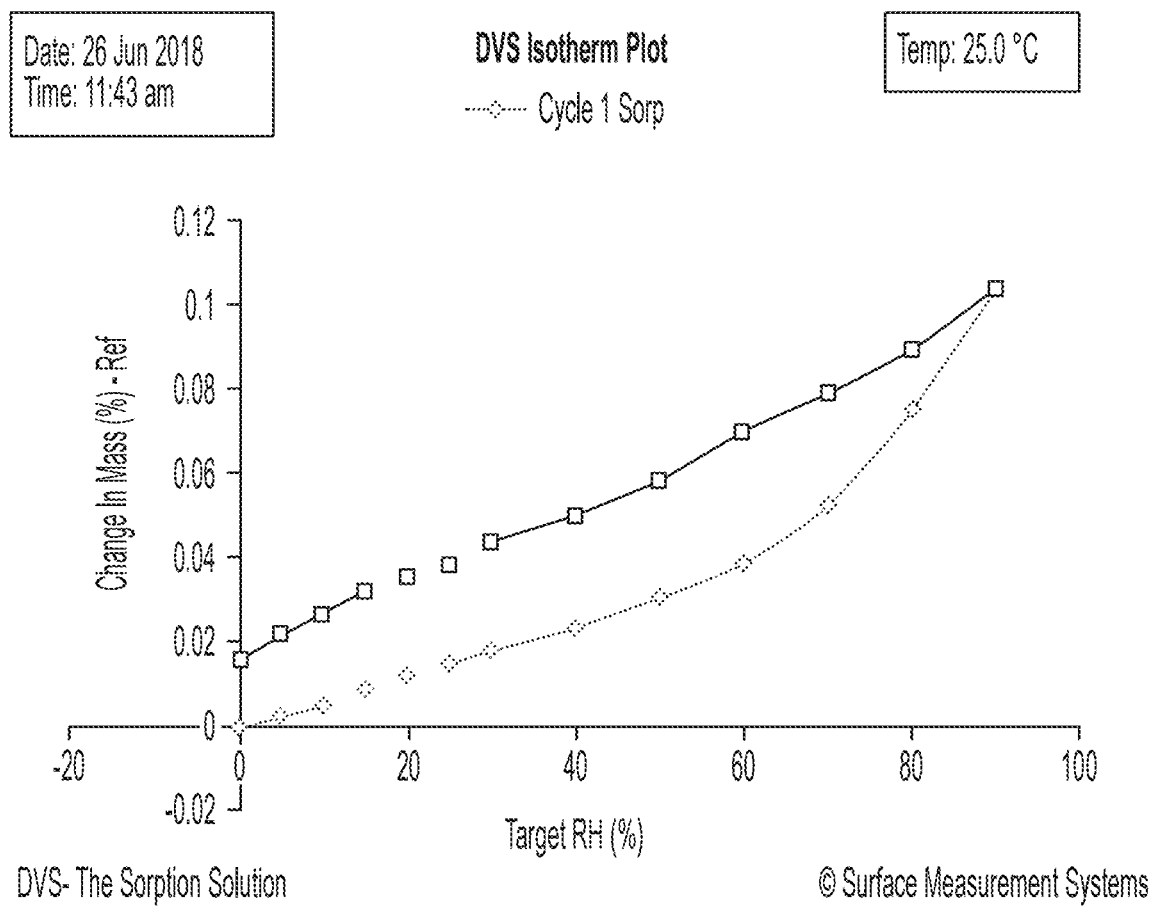
FIG. 14A and FIG. 14B show the DVS plot of crystalline Form B of N-hydroxy 2-{6-[(6-fluoro-quinolin-2-ylmethyl)-amino]-3-aza-bicyclo[3.1.0]hex-3-yl}pyrimidine-5-carboxamide.
Figure 14B:
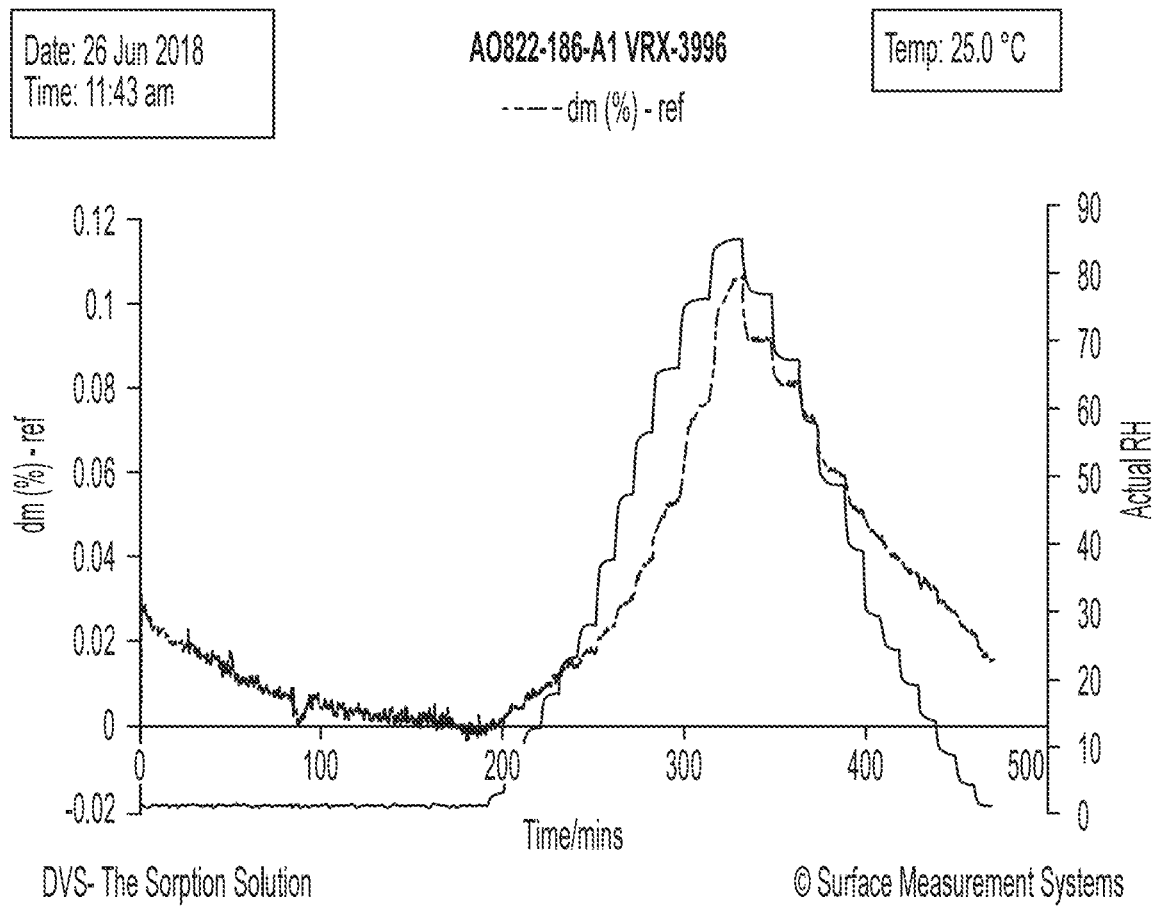
Figure 15:
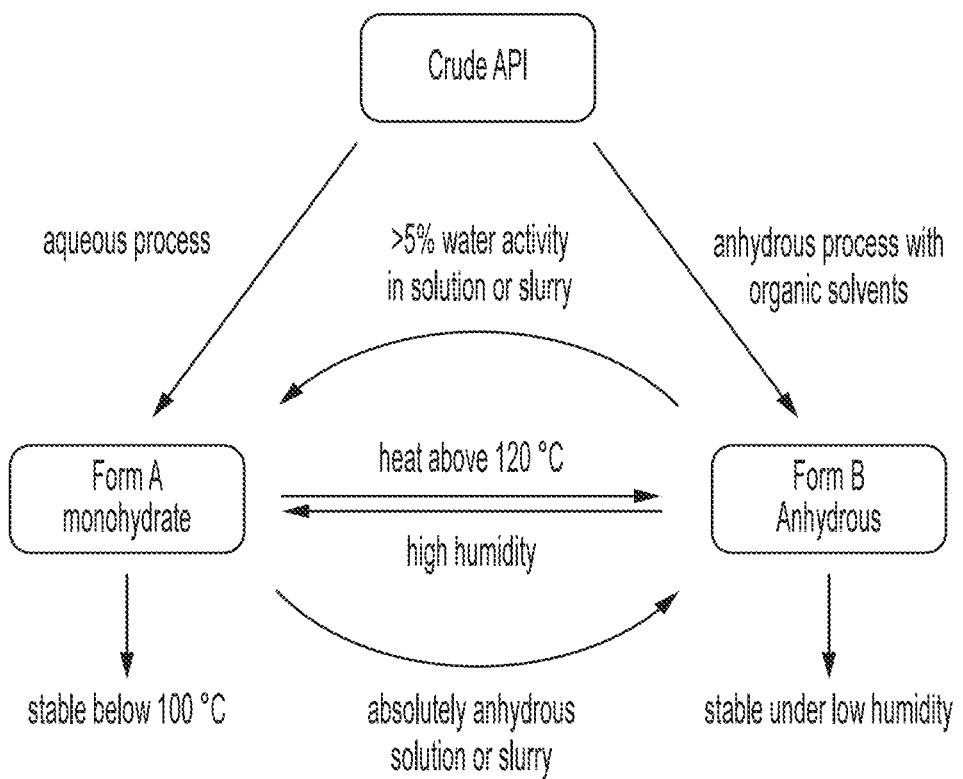
FIG. 15 shows the relationship between crystalline Form A and crystalline Form B of N-hydroxy 2-{6-[(6-fluoroquinolin-2-ylmethyl)-amino]-3-aza-bicyclo[3.1.0]hex-3-yl}pyrimidine-5-carboxamide.

Procedure: First event: a sample of compound 1 Form E (ca. 8 mg) was heated at a rate of +10° C./min from 20 to 160° C. to include the first endothermic event and exclude the second event (refer to FIG. 11). The content of the spent crucible was expressed, the residue was analyzed by XRPD and the diffraction pattern was compared to the input diffraction pattern (see FIG. 12).

The following observations were made:
1. Form E was desolvated by heating above 160° C. The resultant dehydrate was consistent with Form B.
2. Hexafluoropropan-2-ol was not detected by 41 NMR confirming the desolvation of Form E.
3. The weight loss transition that corresponded to desolvation was greater than the amount of the amount of hexafluoro-isopropanol present (4.1% w/w), indicating that water was present.

Example 7: Crystallization Screen by Vapor Diffusion Technique

Objective: Vapor diffusion is a useful technique employed to promote crystallization by altering the composition of the solution of solute.

Procedure: Saturated solutions of compound 1 Form A were prepared in the appropriate, less volatile solvent (2 ml) and clarified through a 2 μm PTFE membrane to remove any crystalline legacy. The concentrated solutions were then placed into separate vessels and each vessel was placed within a larger vessel. Volatile precipitant solvent (diethyl ether) was added to the larger vessel to form a moat around the outside of the smaller vessel, the larger vessel was then capped. The vessel set-ups were allowed to stand undisturbed for several days at 18 to 23° C. During which time, the volatile solvent diffused across into the smaller vessel and promoted crystallization of compound 1. The isolated products were collected by filtration and oven dried at 40° C. under reduced pressure for ca 20 h. The results are provided in Table 6.

TABLE 6

| Crystallization Solvent | Precipitant solvent | Observation t = 96 h | yield % th | Form by XRPD |
|---|---|---|---|---|
| Hexafluoropropan-2-ol | Ether | Solid | 99% | Form E (4.1% w/w) |
| Trifluoroethanol/water (6.7/1 v/v) | Ether | Solid | 14% | Form A |

The following observations were made:
1. The product obtained from hexafluoropropan-2-ol/ether crystallization exhibited a different diffraction pattern than Forms A to D and was designated as Form E
2. The form is disordered and therefore not a single phase and is likely to contain amorphous aspects optically and when imaged under SEM
3. Form A was obtained from trifluoroethanol/water/ether (6.7/1 v/v).

Example 8: Crystallization Screen Via Ballistic Cooling

Objective: Crystallization screen incorporating ballistic/quench cooling to kinetically stress the substrate and analyze immediately following isolation.

Procedure: Separate, pre-weighed portions of compound 1 Form A (ca. 50 mg) were dissolved in the appropriate solvent at temperature. Once dissolved, the vials containing the hot solutions were quenched into ice water, achieving an effective cool rate of several thousand deg C./minute. Each vial was allowed to stand undisturbed for ca 2 min at this temperature. Any solids that formed were isolated as soon as possible by filtration under nitrogen, off-loaded from the filtration assembly and analyzed by XRPD. The results are provided in Table 7.

TABLE 7

| Solvent component A (20 vol, 1000 μl) | ICH Class | Solvent component B | Solvent component B (μl) | Observation | Yield % th., not corr. | Output form (XRPD) |
|---|---|---|---|---|---|---|
| Acetone | 3 | Water | 1000 | Not dissolved | N/A | N/A |
| Acetonitrile | 2 | Water | 1020 | Solid | 77% | Form A |
| Butanol | 3 | Water | 1000 | Solid | 99% | Form A |
| 1,4-dioxane | 2 | Water | 190 | Solid | 33% | Form A |
| Ethanol | 3 | Water | 1000 | Solid | 88% | Form A |
| Methanol | 2 | Water | 1000 | Not dissolved | N/A | N/A |
| Methyl acetate | 3 | Water | 1000 | Solid | 68% | Form A |
| Methylethyl ketone | 3 | Water | 1000 | Solid | 50% | Form A |
| 2-Propanol | 3 | Water | 1000 | Solution | 70% | Form A |
| Propionitrile | — | Water | 1000 | Solid | 99% | disordered Form A |
| Tetrahydrofuran | 2 | Water | 210 | No solid | 76% | Form A |

The following observations were made:

1. The majority of the products isolated were consistent with the Form A, so the dominant form under kinetic conditions at high water activity is Form A.

Example 9: DVS Analyses

DVS analysis was performed on compound 1 Form A and compound 1 Form B to determine the degree of hygroscopicity. The results are provided in FIGS. 13A, FIG. 13B, FIG. 14A and FIG. 14B. Hygroscopicity classification as defined by the European Pharmacopeia is provided in Table 8.

TABLE 8

| Classification | % water uptake at 25° C./80% RH (w/w) |
|---|---|
| Non-hygroscopic | 0-0.12 |
| Slightly hygroscopic | 0.2-2 |
| Moderately hygroscopic | 2.0-15.0 |
| Very hygroscopic | >15 |

The following observations were made:

1. Neither form exhibited a form change during DVS treatment.
2. Form A lost ca 0.25% w/w during the pre-equilibration, whilst Form B lost 0.03% w/w.
3. Both forms exhibited low reversible moisture affinities Form B<Form A, with neither being hygroscopic.
4. Treatment of Form B at 40° C. at high water activity promoted the conversion into Form A.

Example 10: Competitive Suspension Equilibrations

Objective: Determine the fates of the Form A and Form B when equilibrated in ethanol under anhydrous and aqueous conditions at 20° C. and 40° C.

Procedure: Composites, prepared from equimolar amounts of Form A and Form B were charged to separate vials and ethanol (13 vol) or ethanol/water (10/3 v/v, 13 vol) were added. The two pairs of mixtures were stirred at 20° C. or 40° C. overnight.

Results are provided in Table 9.

TABLE 9

| Solvent (10 vol) | Temp (° C.) | Composite input form (XRPD) | Output form (XRPD) | Yield th % |
|---|---|---|---|---|
| Ethanol | 20 | Form A + Form B (1/1 w/w) | B (Major component phase) + A | 83% |
| Ethanol | 40 | Form A + Form B (1/1 w/w) | Form B | 91% |
| Ethanol/water (10/3 v/v) | 20 | Form A + Form B (1/1 w/w) | Form A | 83% |
| Ethanol/water (10/3 v/v) | 40 | Form A + Form B (1/1 w/w) | Form A | 98% |

The following observations were made:

1. When stirred under anhydrous conditions at 20° C., composite Form A+B, underwent near complete conversion into Form B and the product contained only a small proportion of Form A by XRPD.
2. Under anhydrous conditions at 40° C., complete turnover into single Form B was observed after 20 h.
3. Treatment under aqueous conditions at both 20° C. and 40° C. converted composite Form A+B into single Form A.
4. No rigid conversion temperature was observed between 20° C. and 40° C., other than accelerating the rate of conversion as the temperature was increased.
5. Form B is the stable single polymorph under anhydrous slurry bridge conditions and Form A (hydrate) can be fully converted into Form B. Note: earlier investigations demonstrated that Form A undergoes thermally induced dehydration into Form B.
6. Form A is a stable stoichiometric hydrate and the preferred form under conditions of high water activity. Form B will convert into Form A under these conditions. Form A is not hygroscopic by DVS.

Example 11: Suspension Equilibration of Single Form A and B Under Production Conditions Objective: Determine the fates of single Form A and B when equilibrated in ethanol under anhydrous and aqueous conditions at 40° C.

Procedure: Form B and Form A were charged to separate vials. Ethanol/water (10/3 v/v, 13 vol) and ethanol (13 vol) were added, respectively. The mixtures were stirred at 20° C. or 40° C. overnight.

Results are provided in Table 10.

TABLE 10

| Solvent (10 vol) | Temp (° C.) | Composite input form (XRPD) | Output form (XRPD) | Yield th % |
|---|---|---|---|---|
| Ethanol/water (10/3 v/v) | 40 | Form B (A0822-170-AC1) | A + B | 72% |
| Ethanol | 40 | Form A (A0822-170-AD1) | Form B | 70% |

The following observations were made:
1. Under anhydrous conditions at 40° C., Form A converted to Form B. This is consistent with the previous results.
2. Treatment under aqueous conditions at 40° C. converted Form B to the mixture Form A and B, Form B was the major component.

Example 12: Crystallization from Ethanol/Water, Seeded with Form B

Objective: Determine the physical form of compound 1 Form A after crystallization from ethanol/water (1/1 v/v, 40 vol) seeded with Form B.

Procedure: Compound 1 Form A (49.7 mg, 1.0 wt) was charged to separate scintillation vials. To the vial was added the ethanol/water (1/1 v/v, 40 vol), the vials were capped and the suspensions were heated (>100° C.) until full dissolution occurred. The solution was cooled down, seeds of Form B (2.4 mg, 5% w/w) were charged. Stirring was suspended and the solution was removed from the heat, allowed to cool slowly and left to stand undisturbed. The product (16.5 mg, 32% th.) crystallized and was isolated by filtration, deliquored under a stream of nitrogen and dried at 40° C. under reduced pressure over ca. 20 h.

The following observations were made:
1. Form A seeded with Form B, crystallized as Form A at high water activity, therefore, not possible to generate anhydrous Form B from aqueous crystallization.

Example 13: Preparation of Form B

Procedure 1: Compound 1 (500-750 mg, Form A) was suspended and dissolved the selected solvent at 50° C. as shown in Table 11. Separately, acetone was pre-cooled at 5° C. and the solutions containing compound 1 were pipetted into the cold acetone solutions with stirring. The samples were left to stir at 5° C. overnight. Table 11 details the amount of API used and the selected solvents and volumes for antisolvent addition.

TABLE 11

Procedure for Form B and Pattern 4 scale-up

| Amount of API | Solvent (volume) | Anti-solvent (volume) | Observation on addition of solvent to anti-solvent | Observation after stirring at 5° C. |
|---|---|---|---|---|
| 500 mg | Trifluoroethanol (20 vol, 10 ml) | Acetone (50 vol, 25 ml) | Turbid solution became more turbid | White suspension formed a few minutes after initial addition |
| 500 mg | DMSO (10 vol, 5 ml) | Acetone (50 vol, 25 ml) | Clear solution turned slightly orange | White suspension had formed by the following day |

Procedure 2: Form A solid was heated to ~120° C. under dry N2 for extended time and cooled back to room temperature to afford form B.

Procedure 3: A suspension or solution (dependent on concentration) of form A or crude API was stirred in anhydrous EtOAc at 50° C. for extended time and cooled back to room temperature to afford form B.

Example 14: Single Crystal X-Ray Crystallographic Analysis of Form A and Form B

Description of Equipment and Data Collection

Rigaku Oxford Diffraction XtaLAB Synergy four-circle diffractometer equipped with a HyPix-6000HE area detector.

Cu: $\lambda$=1.54184 Å, 50 W, Micro focus source with multilayer mirror ($\mu$-CMF).

Distance from the crystal to the CCD detector: d=35 mm
Tube Voltage: 50 kV
Tube Current: 1 mA Form A A total of 17420 reflections were collected in the 2θ range from 7.298 to 133.18. The limiting indices were: $-5 \leq h \leq 7$, $-15 \leq k \leq 14$, $-15 \leq l \leq 15$; which yielded 3379 unique reflections (Rint=0.0238). The structure was solved using SHELXT (Sheldrick, G. M. 2015. Acta Cryst. A71, 3-8) and refined using SHELXL (against F2) (Sheldrick, G. M. 2015. Acta Cryst. C71, 3-8). The total number of refined parameters was 279, compared with 3379 data. All reflections were included in the refinement. The goodness of fit on F2 was 1.056 with a final R value for [I>2σ (I)] R1=0.0356 and wR2=0.0977. The largest differential peak and hole were 0.18 and −0.20 Å-3, respectively.

FIG. 16 provides a summary of the X-ray crystallographic data for form A monohydrate.

Figure 17A:
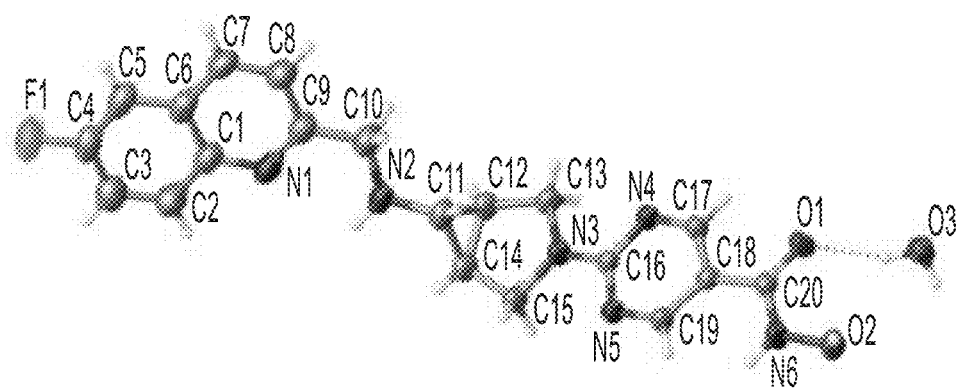
FIGS. 17A and 17B shows the ORTEP diagram and crystal packing of crystalline Form A monohydrate.
Figure 17B:
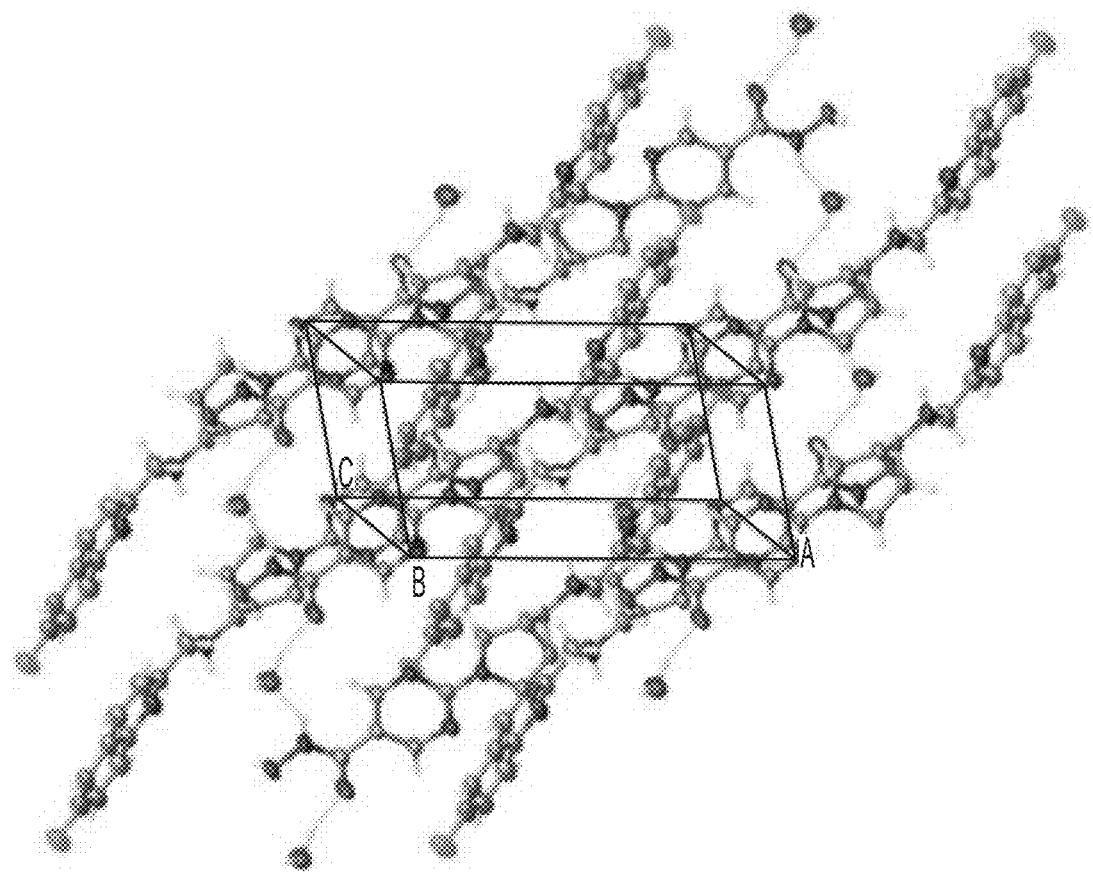

FIG. 17A provides the ORTEP diagram of the form A monohydrate and FIG. 17B illustrates the stacking of molecules in the crystal.

Form B

A total of 30813 reflections were collected in the 2θ range from 7.056 to 133.1. The limiting indices were: $-6 \leq h \leq 6$, $-14 \leq k \leq 14$, $-14 \leq l \leq 14$; which yielded 3029 unique reflections (Rint=0.0469). The structure was solved using SHELXT (Sheldrick, G. M. 2015. Acta Cryst. A71, 3-8) and refined using SHELXL (against F2) (Sheldrick, G. M. 2015. Acta Cryst. C71, 3-8). The total number of refined parameters was 263, compared with 3029 data. All reflections were included in the refinement. The goodness of fit on F2 was 1.074 with a final R value for [I>2σ (I)] R1=0.0370 and wR2=0.0999. The largest differential peak and hole were 0.47 and −0.45 Å-3, respectively.

FIG. 18 provides a summary of the X-ray crystallographic data for form B.

Figure 19A:
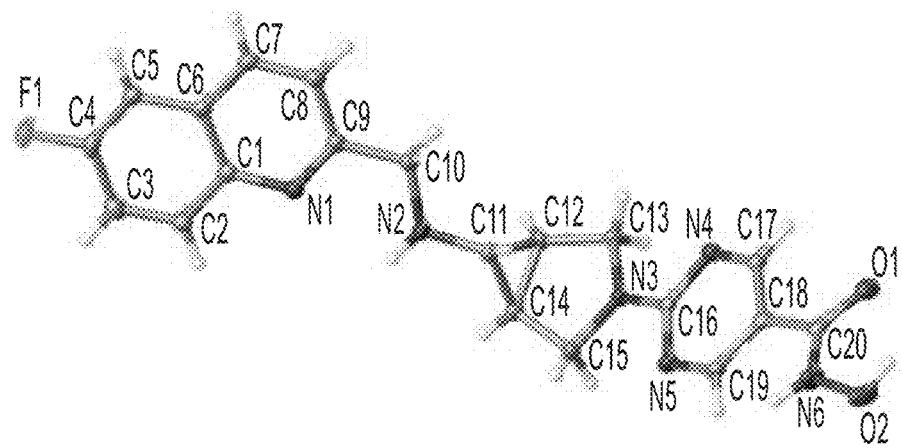
FIGS. 19A and 19B shows the ORTEP diagram and crystal packing of crystalline Form B.
Figure 19B:
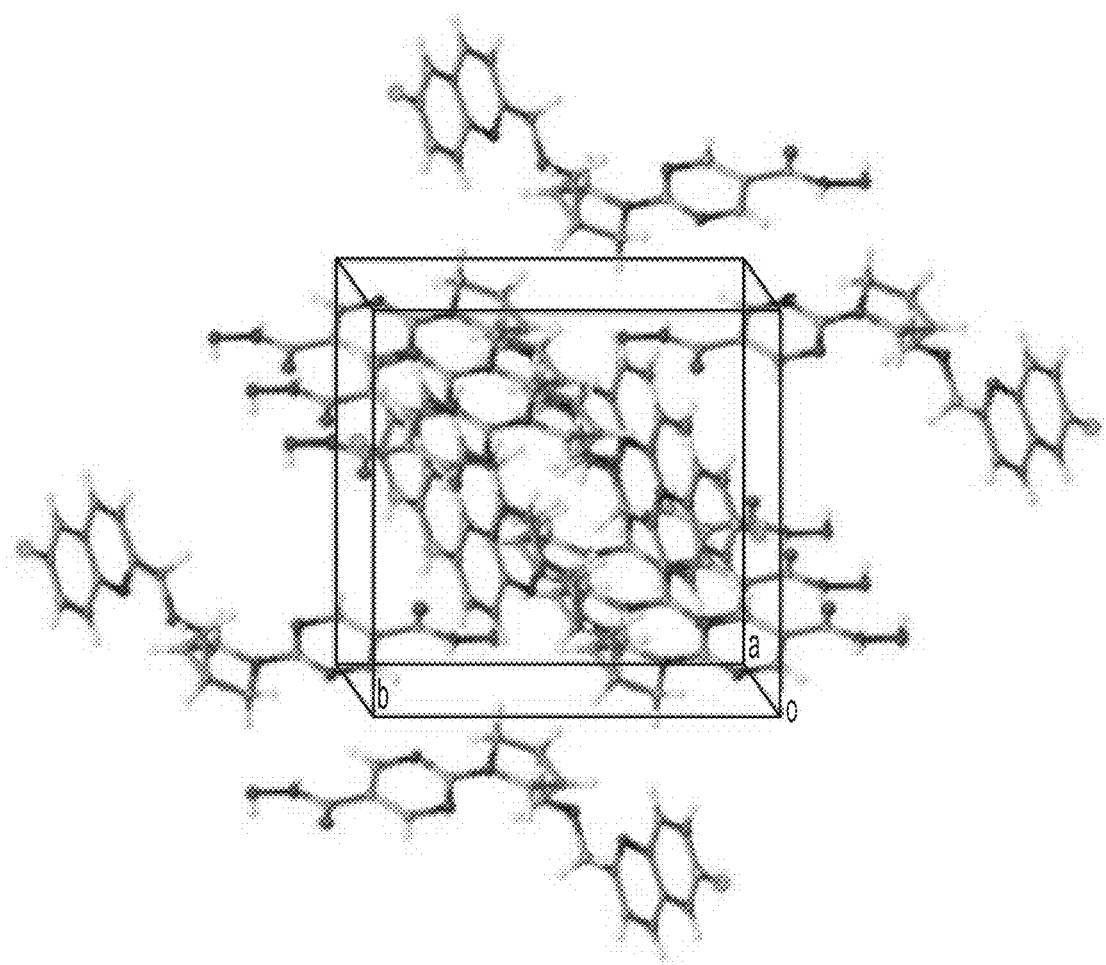

FIG. 19A provides the ORTEP diagram of the form A monohydrate and FIG. 19B illustrates the stacking of molecules in the crystal.

III. Pharmaceutical Dosage Forms

Example 1: Processes for Making Pharmaceutical Dosage Form

Capsules, 5 mg, were manufactured according to cGMP using standard processes in premises suitable for the manufacture of pharmaceutical products. Table 12 provides a batch formula for preparing 5 mg capsules.

TABLE 12

| Component | Amount (g) | % |
|---|---|---|
| Compound 1[1] | 134.0 | 2.50 |
| Silicified Microcrystalline Cellulose (Prosolv HD90) | 4841.0 | 97.00 |
| Sodium Stearyl Fumarate | 25.0 | 0.50 |
| TOTAL | 5000.0 | 100.0 |
| Gelatin Capsules, Size 2, White Opaque[2] | 1525.0 | — |
| TOTAL | 6525.0 | — |

[1]Actual amount is corrected for drug substance purity (CoA)
[2]Based on average capsule weight provided by manufacturer Mixing of the dry blend was conducted on five approximately equal-sized portions as follows. Compound 1 drug substance, Prosolv HD90 (silicified microcrystalline cellulose) and sodium stearyl fumarate were individually passed through 30-mesh screens to remove and break down any lumps that might be present. Approximately half of the Prosolv HD90 for each portion (10% of total amount for the batch) was added to a 4-L GMX-LAB Micro high-shear mixer, followed by compound 1 and sodium stearyl fumarate (each 20% of total amount for batch). The remainder of the Prosolv HD90 for the portion was then added to the mixer bowl.

The dry blend was mixed at 950±50 rpm for 20±1 minutes, and then the blend was transferred to a Bohle LM-40 blender with 20-L bin. Once all five of the blend portions had been processed and loaded into the Bohle blender, the final blend was mixed at 25 rpm for 20±1 minutes. Samples are taken with a sample thief and submitted for blend uniformity (BU) testing.

The final blend was filled into Size 2, white opaque, hard gelatin capsule shells using a Torpac Profill capsule filler. The capsules are polished/dedusted using a Key TD101-EWD deduster, then weighed using a Sade SP checkweigher. Capsules outside of the target weight action limits were rejected and discarded. Acceptable capsules were collected in bulk into double-layer plastic bags inside of rigid containers.

Example 2: Processes for Making Pharmaceutical Dosage Form

Table 13 provides a batch formula for preparing capsules of various dosage strength.

TABLE 13

| Component | Quantity (mg/capsule) | | | | |
|---|---|---|---|---|---|
| Compound 1[1] | 2.5 | 5.0 | 10.0 | 20.0 | 40.0 |
| Dibasic calcium phosphate dihydrate[2] | 315.5 | 313.00 | 308.00 | 298.00 | 278.00 |
| Microcrystalline Cellulose | 80.00 | 80.00 | 80.00 | 80.00 | 80.00 |
| Magnesium Stearate | 2.00 | 2.00 | 2.00 | 2.00 | 2.00 |
| Total fill weight | 400 | 400 | 400 | 400 | 400 |
| White to Off-White Hard Gelatin Capsule Shell | n/a | n/a | n/a | n/a | n/a |

[1]Amount of compound 1 is adjusted for purity based on Certificate of Analysis for batch
[2]Exact amount of dibasic calcium phosphate dihydrate to be adjusted to account for purity-adjusted amount of Compound 1 added Hard gelatin capsules of compound 1 were manufactured according to GMP using standard pharmaceutical processes in premises suitable for the manufacture of pharmaceutical products.

Each of the excipients and compound 1 were individually passed through a screen in order to remove and break down any lumps that might be present. Compound 1 and approximately one third to one half of the microcrystalline cellulose were mixed together and then the remaining microcrystalline cellulose added and mixed into the blend. Approximately one third to one half of the calcium phosphate was then added to the compound 1/microcrystalline cellulose blend and mixed. The remaining calcium phosphate was then added and mixed into the compound 1 blend. Approximately 50 g of the resulting compound 1 blend was then removed and added to a separate container which holds the screened magnesium stearate and the powders were mixed. The compound 1/magnesium stearate blend was then added back into the bulk compound 1/microcrystalline cellulose/calcium phosphate blend and mixed further. The blend was filled into size 1, white to off-white, opaque, hard, gelatin capsule shells.

Example 3: Processes for Making Pharmaceutical Dosage Form

Table 14 provides a batch formula for preparing film-coated immediate release tablets.

TABLE 14

| Component | Function | % w/w | 5-mg strength (mg/tablet) | 10-mg strength (mg/tablet) |
|---|---|---|---|---|
| VRx-3996 | Drug substance | 5.0 | 5 | 10 |
| Mannitol | Filler | 25.0 | 25 | 50 |
| Microcrystalline cellulose | Filler | 65.5 | 65.5 | 131 |
| Croscarmellose sodium | Disintegrant | 4.0 | 4.0 | 8.0 |
| Sodium stearyl fumarate | Lubricant | 0.5 | 0.5 | 1.0 |
| Total (core) | | 100 | 100 | 200 |
| Opadry II coating powder | Film coating | 3.0 | 3.0 | 6.0 |
| Water* | Film coating | — | — | — |
| Total | | | 103 | 206 |

*used to form solution and removed during processing

The homogeneity of the powder blend was tested during the mixing process just prior to the addition of the magnesium stearate and prior to filling the capsules. Capsule fill weights were checked during the filling process and a 100% capsule weight check was performed at the end of the filling run.

We claim:

1. Crystalline hydrate Form A of N-hydroxy 2-{6-[(6-fluoro-quinolin-2-ylmethyl)-amino]-3-aza-bicyclo[3.1.0]hex-3-yl}pyrimidine-5-carboxamide.

2. The crystalline hydrate of claim 1, characterized by an X-ray diffraction pattern reflection at a 2 theta value of 15.9.

3. The crystalline hydrate of claim 2, further characterized by an X-ray diffraction pattern reflection at a 2 theta value of 21.7.

4. The crystalline hydrate of claim 2, further characterized by X-ray diffraction pattern reflections at 2 theta values of 29.1 or 23.2.

5. The crystalline hydrate of claim 2, further characterized by X-ray diffraction pattern reflections at 2 theta values of 21.7, 29.1, and 23.2.

6. The crystalline hydrate of claim 2, further characterized by X-ray diffraction pattern reflections at 2 theta values of 21.7, 29.1, 23.2, 24.1, and 26.7.

7. The crystalline hydrate of claim 2, further characterized by at least one X-ray diffraction pattern reflection selected from a 2 theta value of 21.7, 29.1, 23.2, 24.1, and 26.7.

8. The crystalline hydrate of claim 2, further characterized by at least three X-ray diffraction pattern reflections selected from a 2 theta value of 21.7, 29.1, 23.2, 24.1, and 26.7.

9. The crystalline hydrate of claim 1, further characterized by an X-ray diffraction pattern reflection at a 2 theta value of 21.7.

10. The crystalline hydrate of claim 9, further characterized by X-ray diffraction pattern reflections at 2 theta values of 29.1 or 23.2.

11. The crystalline hydrate of claim 9, further characterized by at least one X-ray diffraction pattern reflection selected from a 2 theta value of 15.9, 29.1, 23.2, 24.1, and 26.7.

12. The crystalline hydrate of claim 9, further characterized by at least three X-ray diffraction pattern reflections selected from a 2 theta value of 15.9, 29.1, 23.2, 24.1, and 26.7.

13. The crystalline hydrate of claim 1, exhibiting the X-ray powder diffraction pattern as shown in FIG. 1.

14. The crystalline hydrate of claim 1, exhibiting the differential scanning calorimetry thermogram as shown in FIG. 2.

15. The crystalline hydrate of claim 1, exhibiting an endothermic peak at about 153° C. as determined by differential scanning calorimetry.

16. The crystalline hydrate of claim 1, exhibiting an exothermic peak at about 215° C. as determined by differential scanning calorimetry.

17. The crystalline hydrate of claim 1, exhibiting the thermogravimetric analysis thermogram as shown in FIG. 3.

18. The crystalline hydrate of claim 1, exhibiting a mass loss of at least 4% upon heating from 30° C. to 150° C. as determined by thermogravimetric analysis.

19. The crystalline hydrate of claim 1, exhibiting a mass loss of at least 14% upon heating from 30° C. to 245° C. as determined by thermogravimetric analysis.

20. A pharmaceutical composition comprising the crystalline hydrate of claim 1, and one or more pharmaceutically acceptable excipients or carriers.

* * * * *